(12) United States Patent
Zoth et al.

(10) Patent No.: US 7,922,671 B2
(45) Date of Patent: Apr. 12, 2011

(54) METHOD AND APPARATUS FOR AUTOMATIC NON-COOPERATIVE FREQUENCY SPECIFIC ASSESSMENT OF HEARING IMPAIRMENT AND FITTING OF HEARING AIDS

(75) Inventors: Peter Zoth, Gilching (DE); Thomas Janssen, Tuntenhausen (DE)

(73) Assignee: Natus Medical Incorporated, San Carlos, CA (US)

( * ) Notice: Subject to any disclaimer, the term of this patent is extended or adjusted under 35 U.S.C. 154(b) by 968 days.

(21) Appl. No.: 11/650,657

(22) Filed: Jan. 8, 2007

(65) Prior Publication Data
US 2007/0156063 A1    Jul. 5, 2007

Related U.S. Application Data

(63) Continuation-in-part of application No. 10/353,350, filed on Jan. 29, 2003, now Pat. No. 7,223,245.

(60) Provisional application No. 60/352,966, filed on Jan. 30, 2002.

(51) Int. Cl.
*A61B 5/00* (2006.01)
*A61B 5/04* (2006.01)
*A61B 5/12* (2006.01)

(52) U.S. Cl. ........ 600/559; 600/372; 600/373; 600/379; 600/544; 73/585

(58) Field of Classification Search .................. 600/559, 600/372, 379, 378, 382, 383, 544, 545, 547; 73/585, 584
See application file for complete search history.

(56) References Cited

U.S. PATENT DOCUMENTS

| 5,999,856 A | 12/1999 | Kennedy |
| 6,167,138 A | 12/2000 | Shennib |
| 6,602,202 B2 | 8/2003 | John et al. |

*Primary Examiner* — Jeffrey G Hoekstra
(74) *Attorney, Agent, or Firm* — Temmerman Law Office; Mathew J. Temmerman

(57) ABSTRACT

A method and device for automatically assessing loss of hearing sensitivity and compression (recruitment) with user defined frequency resolution by means of extrapolated DPOAE I/O functions and ABRs as well as for automatically fitting hearing aids without any cooperation of the subject tested using a device having a display screen attached to a handheld device generating and collecting otoacoustic emission signals and brain stem response signals into a programmed with a clinical audiogram with fitting parameters for hearing aids calculated on the basis of assessed hearing threshold and compression and identifying the type of hearing required for the individual.

43 Claims, 17 Drawing Sheets

Fig. 4
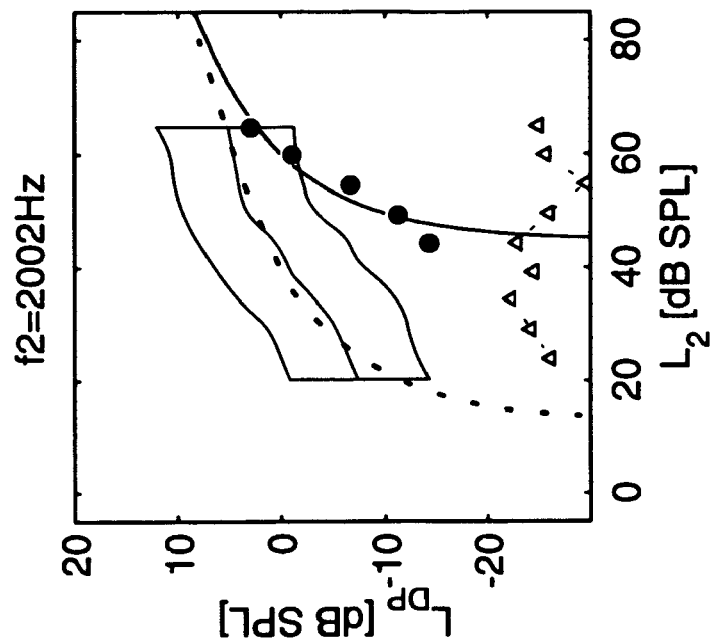
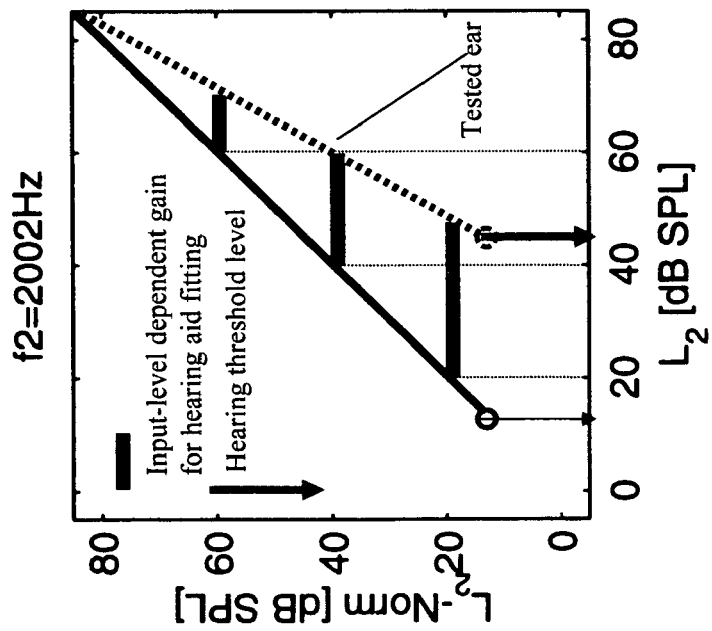

Fig. 16
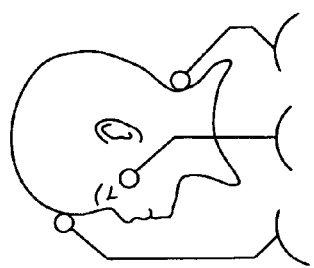
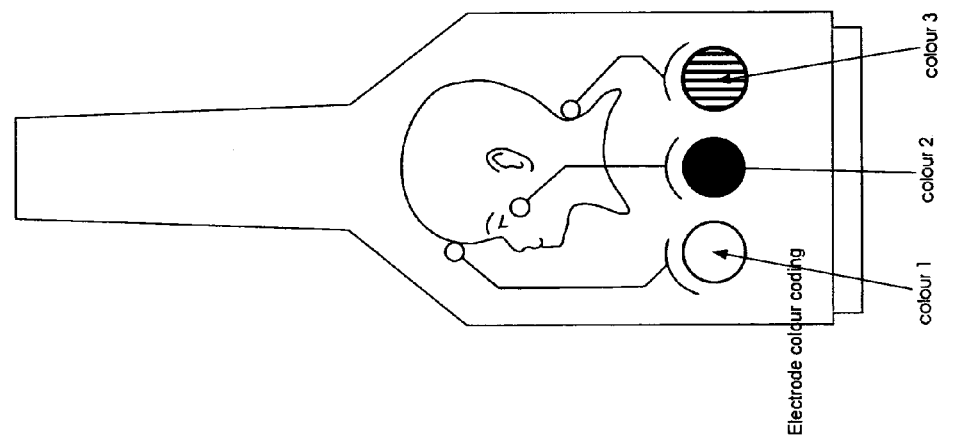

METHOD AND APPARATUS FOR AUTOMATIC NON-COOPERATIVE FREQUENCY SPECIFIC ASSESSMENT OF HEARING IMPAIRMENT AND FITTING OF HEARING AIDS

RELATED APPLICATIONS

This application is a continuation-in-part application of the formal patent application Ser. No. 10/353,350 entitled "Method and Apparatus for Automatic Non-Cooperative Frequency Specific Assessment of Hearing Impairment and Fitting of Hearing Aids" filed Jan. 29, 2003, now U.S. Pat. 7,223,245, which is a continuation-in-part of the Provisional Patent Application Ser. No. 60/352,966 entitled "Method and Apparatus for Automatic Non-Cooperative Frequency Specific Assessment of Hearing Impairment and Fitting of Hearing Aids" filed Jan. 30, 2002.

BACKGROUND OF THE INVENTION

1. Field

This invention pertains to hearing testing and hearing aid fitting devices. In particular it pertains to a hearing testing device employing means of extrapolated distortion product otoacoustic emission input/output functions (DPOAE I/O-functions) and/or auditory brain stem responses (ABRs) as well as for automatically fitting hearing aids without any cooperation of the subject tested using a device having a display screen attached to a handheld device generating and collecting otoacoustic emission signals and/or brain stem response signals into a programmed computer with a clinical audiogram providing fitting parameters for hearing aids calculated on the basis of assessed hearing threshold and compression. In addition tympanometry and ABR-Inter-Peak-Latency assessment (ABR-IPL) for differentiating middle-ear, cochlear and neural disorders can be optionally performed.

2. State of the Art

Psycho acoustical tests are commonly used for assessing hearing threshold. These tests are not successful with patients that cannot communicate responses, such as neonates, and require skilled testers who can interpret the responses. Furthermore, psycho acoustical tests need a lot of time to assess disturbances of sound processing. As a result, objective measurements for assessing hearing loss have been developed. Conventionally, behavioral hearing threshold is represented as hearing loss in a clinical audiogram form at different frequencies, usually at 125, 250, 500, 1000, 2000, 4000, and 8000 Hz. In principal, also ABRs and OAEs are potential measures for assessing hearing loss. The advantage of these measures over behavioral hearing testing is that they are "objective" in the sense that no cooperation of the patient is needed, and therefore can be used in infants and young children. Furthermore, objective measurements allow more precise identification of hearing impairment in a shorter time. Thus, they are also suited for hearing testing in adults. Behavioral threshold and the latency and amplitude of ABRs and the distortion product otoacoustic emission (DPOAE) sound pressure level and the slope of the DPOAE I/O-function, respectively, are reported to be closely related (Jacobson 1985, Janssen et al. 1998, Kummer et al. 1998). Various measurements devices have been employed to measure these responses. However, they also require trained testers, and elaborate equipment. The device and method described below provides an easy to use handheld hearing testing device, which also provides hearing aid fitting parameters which are calculated on the basis of the assessed loss of hearing and compression. The fitting of the hearing aid is performed automatically after identifying the type of the hearing aid and loading the respective software for adjusting the hearing aid.

SUMMARY OF THE INVENTION

The present invention provides a method and handheld apparatus to assess the loss of hearing sensitivity and compression (recruitment) by means of physiological measures, particularly by otoacoustic emissions (OAEs) and/or auditory brain stem responses (ABRs). Otoacoustic emissions (OAE's) are generated in the cochlea They reflect the movement of outer hair cells when stimulated acoustically. Both stimulus and response are of acoustic nature. Transient Evoked Otoacoustic Emissions (TEOAE) are elicited by transient stimuli (clicks, tone-bursts); Distortion Product Otoacoustic Emissions (DPOAE) by two tones with a distinct frequency ratio. Auditory evoked potentials (AEPs) are electrical responses generated on the auditory pathway between cochlea and brain measured from electrodes fixed on the human scalp. Auditory brain responses (ABRs) are elicited by transient stimuli (clicks, tone-bursts); Auditory steady state responses (ASSRS) by amplitude modulated tones. Thus, OAE and AEP are quite different. The first original articles on OAE and ASSR discussing these differences are: Kemp DT (1978) Stimulated acoustic emissions from within the human auditory system. J Acoust Soc Am 64:1386-1391 and Galambos et al. (1981) A 40-Hz auditory potential recorded from the human scalp. Proceedings of National Academy of Science USA, 78, 2643-2647.

OAEs and ABRs, which, when used together, form a powerful tool to provide information about the workings of the middle ear, cochlear, and retro-cochlear sound processing and its disturbances. The invention also utilizes distortion product otoacoustic emission input/output functions (DPOAE I/O-functions), which mirror the sensitivity and non-linear compression of cochlear outer hair cells, amplifying mechanically low intensity sounds, as well as to auditory brainstem responses (ABRs), especially, high click rate evoked ABRs (HCR-ABRs) and amplitude modulated following responses (AMFRs), representing neural sound processing in afferent nerve fibers. The flexibility of the method and device to assess hearing loss and fit hearing aids is more particularly described as follows:

Assessment of Sensitivity and Compression of Outer Hair Cell Amplifiers by Means of Weighted Extrapolated DPOAE I/O-Functions (DPOAE Cochlea-Scan)

DPOAEs are the only non-invasive physiological measure offering evaluation of hearing with high frequency resolution. DPOAEs are low-level sounds that emanate from the cochlea representing the mechanical distortion of outer hair cells within the region of overlap of the two primary tones with frequencies f1 and f2 and sound pressure levels L1 and L2 and can be recorded from the external ear canal using sensitive low-noise microphones (Kemp 1978, Lonsbury-Martin 1997, U.S. Pat. No. 5,664,577). Due to stationary stimulation (pure tones) only a small area of the cochlea is stimulated. Thus, DPOAEs provide a high frequency-resolution scanning of cochlear function when elicited at different frequencies. Today, DPOAE cannot be measured at very low stimulus levels due to biological and technical noise and therefore no direct assessment of hearing threshold is possible. However, using extrapolated DPOAE I/O-functions hearing threshold can indirectly be determined. Since DPOAE sound pressure is a linear function of the sound pressure level when using a primary tone level setting that accounts for the different compression of the two primaries at the generation site of the cochlea, at the f2-place (e.g. L1=0.4 L2+39, see Kummer et al. 2000), DPOAE sound pressure I/O-functions can be easily fitted by linear regression analysis and thus the intersection of the regression line with the primary tone level axes provides the primary tone level which would generate a DPOAE at the hearing threshold (Janssen et al. 2000, EP1027863A1, DE 19905743A1).

Using the primary tone level setting $L_1=0.4 \cdot L_2+39$ dB in most of the DPOAE I/O-functions a logarithmic dependency of the distortion product sound pressure $p_{DP}$ on the sound pressure p2 of the f2 primary tone was found. In semi logarithmic scale this gives a linear dependency between $p_{DP}$ and the primary tone level $L_2$. In FIG. 1a, the DPOAE sound pressure $P_{DP}$ (upper panel) and the DPOAE sound pressure level $L_{DP}$ (lower panel) of the same DPOAE I/O-function are plotted as a function of the primary tone level $L_2$. The linear fit to the data (solid line) proves the logarithmic dependency of $p_{DP}$ on p2. The correlation coefficient r 2 gives a measure of the accuracy of the linear fit. The vertical bar marks in FIG. 1a indicate the estimated DP threshold level $L_{EDPT}$ in both panels. The estimated DPOAE threshold level $L_{EDTP}$ is the extrapolated value equivalent to the primary tone level $L_2$ that would give a zero DPOAE sound pressure $p_{DP}$ and is closely related to hearing threshold (Boege and Janssen 2002, see also Janssen et al. 2000, EP1027863A1, DE 19905743A1).

To improve hearing threshold estimation weighted extrapolation can be applied. Using weighted Least Mean Square Extrapolation regression analysis considering signal-to-noise ratio and close to threshold emissions as independent weighting factors the accuracy of the linear fit can be enhanced (Oswald et al. 2002, ARO Meeting, Abstract 1540) as shown in FIG. 1b.

Besides the assessment of hearing threshold, DPOAEs provide information on compression facility of the outer hair cell amplifiers. In most of sensorineural hearing loss ears, the DPOAE sound pressure level decreases with the slope of the DPOAE I/O-function steeping with increasing hearing loss (Kummer et al. 1998, Janssen et al. 1998). There is a strong correlation between DPOAE sound pressure level and behavioral threshold when comparing both measures at the frequency f2 of the higher primary tone. It should be emphasized that the correspondence is getting closer with decreasing primary tone level. However, in some tinnitus ears a poor or even inverse relationship between DPOAE sound pressure level and behavioral hearing threshold occurs, i.e., displayed an increase of DPOAE sound pressure level with increasing hearing loss. The slope of the DPOAE I/O-function, however, increases with increasing hearing loss and, therefore, still correlates with a hearing threshold revealing pathological alteration of the outer hair cell amplifiers in the frequency region of the tinnitus. In these tinnitus ears the slope of the DPOAE I/O-function is alike at the intersection of the regression line with the primary tone level axes provided a primary tone level which coincided well with the hearing loss. That means, in non-tinnitus ears as well as in tinnitus ears, hearing loss can be assessed on the basis of extrapolated DPOAE I/O-functions. Moreover, the slope of the DPOAE I/O-functions offers frequency specific information on how the compression facility is disturbed in hair cell based hearing loss ears.

For recording DPOAEs, a sound probe has to be inserted in the ear canal. After starting the measuring procedure, a respective graph on the screen of the hand-held device instructs the tester to insert the sound probe if it has not been inserted yet. After inserting the sound probe, calibration of sound pressure in the ear canal is automatically performed. Analyzing the pattern of the frequency response, the sound probe's seal is checked automatically. In the event of insufficient seal, the tester is asked to replace the sound probe by displaying a respective graph on the screen. In the event of sufficient seal the distance of the tip of the sound probe to the eardrum is calculated by determining sound pressure maxima. From estimated ear canal lengths and the eardrum impedance estimated using models known from the literature, eardrum acoustic pressure is calculated. The obtained sound pressure distribution is then used as a basis for calculating the loudspeakers' voltage for generating constant primary tone sound pressure level in the front of the eardrum.

The slope of the DPOAE sound pressure I/O-function s=(a/20) µPa/dB is converted to compression factor k=1/s and is calculated for the selected $f_2$ frequencies providing the compression profile k ($f_2$). The obtained hearing loss and compression factor serve for adjusting multi-channel dynamic compression hearing aids where $f_2$ corresponds to respective channel frequencies. Hearing loss and compression are stored and used for automatic hearing aid fitting.

Since middle ear disorders exhibit specific hearing loss and compression, which is different from that found in cochlear hearing loss ear, middle ear and cochlear disorders can be differentiated by evaluating DPOAE measures. In addition, acoustic reflex thresholds can be obtained by assessing changes of the DPOAE level during acoustic reflex stimulation. In the event of the detection of abnormal middle ear function, "middle ear affected" is displayed on the screen of the hand-held device. Otherwise "middle ear not affected" is indicated. In cases where no differentiation is achieved, "middle ear status not specified" is displayed.

A Flow-chart of module "DPOAE Cochlea-Scan" is shown in FIG. 2.

Assessment of Cochlear Sound Processing by Means of ABR and AMFR (ABR Cochlear Scan)

Since OAEs are only able to assess outer hair cell function, the assessment of hearing capability is restricted to moderate hearing loss. In order to expand the assessment to severe hearing loss, ABRs have to be also recorded. ABRs are well-established objective measurement methods. However, the frequency specificity of the current ABR methods (including notched-noise ABR) is restricted. This is due to the fact that the area of the stimulated sensory cells in the cochlea is getting smaller with decreasing the bandwidth of the acoustic stimulus and thus no sufficient neural activity can be yielded. Generally, AMFR may provide more frequency specific information. But today, there is little data of actual experience with patients.

High click rate evoked ABRs (HCR-ABRS) and AMFRs are the only responses of the neural auditory pathway, which can objectively assess hearing loss by evaluating the response' frequency spectrum and thus are suitable for automatically assessing hearing impairment (e.g. Stürzebecher patent application DE 19954666A1 for AMFRs).

ABRs, HCR-ABRs, and/or AMFRs are measured if the calculation of hearing threshold by means of DPOAE I/O-functions is incomplete. This occurs if hearing loss exceeds 40 or 50 dB. The amplitude of high-click rate evoked ABRs and/or AMFR is calculated from the frequency spectrum. Measurement is started with a click stimulus level that corresponds to the maximum hearing loss estimated from DPOAE I/O-functions. Levels are increased (or decreased) in 5 dB steps for finding ABR and/or AMFR thresholds.

Additionally, high-pass noise or notched-noise masked click or tone-pip evoked ABRs are used for assessing hearing loss. However, pattern recognition is necessary for automatically evaluating ABR latency and threshold. There are specific ABR latency and amplitude functions, which can be used for differentiating middle ear and cochlear disorders.

Based upon OAE and ABR measurements, hearing thresholds are constructed and displayed in the audiogram form. Depending on maximum hearing loss, the corresponding area is marked (e.g. highlighted) and thus provides a comment on the degree of hearing loss in addition to hearing threshold.

For recording ABRs, electrodes have to be fixed on the scalp. After starting the measuring procedure, a respective graph on the screen of the hand-held device asks to fix the electrodes on the subject's scalp. After checking the electrodes' impedance, measuring procedure is continued automatically in the event of sufficient conductivity. In the case of insufficient conductivity, the tester win be asked to check the electrodes. For applying stimuli for eliciting ABRs, the same sound probe is used. Calibration of the stimulus' sound pressure is performed corresponding to that used for eliciting DPOAEs.

If neither DPOAEs nor ABRs are recordable, the hearing loss is classified as profound hearing loss. In this case a thorough investigation of the hearing impairment by conventional audiometrics is necessary and a respective comment is displayed.

A Flow-chart of module "ABR Cochlea-Scan" is shown in FIG. 3.

Automatic Non-Cooperative Hearing Aid Fitting (ANC-Hearing Aid Fitting)

The key to successful compensation for hearing loss caused by damaged hair cells is the accuracy with which hearing aids compensate for and match the characteristics of the hearing impairment. This is especially true in recruitment ears. Recruitment describes a phenomenon, which takes place in most sensorineural hearing loss ears. Recruitment is the progressive alleviation of hearing impairment as the sound level increases. A patient with recruitment is deaf to weak sounds, but progressively less deaf to more intense sound. In cases of complete recruitment the patient has the same loudness as that of a normally hearing subject. For compensating the varying degree of recruitment in different frequency regions of the cochlea, a hearing aid is employed which allows simultaneous independent compression in different channels. Today, multi-channel dynamic compression hearing aids try to meet this requirement (Villchur 1996).

The accuracy with which a hearing aid matches the specific hearing impairment in different regions of the cochlea depends on the accuracy with which the loss of sensitivity and compression of the outer hair cell amplifiers can be assessed by audiological testing. DPOAE I/O-functions are reported to be able to quantitatively assess loss of sensitivity and loss of compression of the outer hair cell amplifiers with high frequency resolution (Janssen et al. 1998, Kummer et al. 1998). Thus, DPOAE I/O-functions are able to provide hearing aid fitting parameters to adjust more precisely gain and compression of multi-channel hearing aids. Today, threshold level, most comfortable level, uncomfortable level of hearing and loudness growth results from subjective hearing testing are used for assessing cochlear impairment and for adjusting hearing aids. Obtaining these subjective measures takes more time. Frequency specificity of loudness scaling is worse. Reproducibility is worse as well, compared to objective testing by means of physiological measures like OAEs and ABRs.

After assessing the hearing loss by means of the Cochlea-Scan™ measurement modules "DPOAE Cochlea-Scan" and "ABR Cochlea-Scan", the method and apparatus fit hearing aids automatically after preparing and loading hearing aid specific software. The method and apparatus is especially accurate when used to fit high fidelity dynamic compression hearing aids, which try to compensate loss of sensitivity and loss of compression of the outer hair cell amplifiers, such as in patients with hair-cell-based hearing losses with recruitment, where dynamic compression hearing aids can make low-level signals uniformly and smoothly audible.

An example of how to derive hearing aid fitting parameters from DPOAE I/O-functions is shown in FIG. 4 and is described in detail below.

A Flow-chart of module "ANC-Hearing Aid Fitting" is shown in FIG. 5.

Additional Optional Tests for the Differentiation of Middle Ear, Cochlear, and Neural Disorders (Tympanometry, ABR-IPL)

Not all cases of hearing impairment, middle-ear, hair-cell, and neural based hearing impairment can be differentiated solely by DPOAEs and/or ABRs and thus additional hearing testing is necessary. Tympanometry measures sound reflection from the tympanic membrane, while the operator varies air pressure in the ear canal. Tympanometry aids assessment of the outer and middle ear system, including the Eustachian tube. It is an objective means of analyzing middle ear function by measuring the compliance or freedom of movement of the ossicular chain and estimates middle ear pressure (this needs to be defined as there is no standard dictionary definition in US)(see Jerger and Northern 1980). It provides information on middle-ear disorders exhibiting characteristic tympanogram patterns for the different pathologies (otitis media, Eustachian tube dysfunction, otosclerosis, ossicular discontinuity, cholesteatoma, perforation of the tympanic membrane etc). Also, impedance audiometry can detect eighth nerve disorder by eliciting the acoustic reflex and measuring corresponding impedance change. Differentiation of cochlear and eighth nerve disorder is also possible by evaluating inter-peak latencies of ABR (Jacobson 1985).

For differentiating middle ear and cochlear disorder eardrum impedance (compliance), measurement (tympanometry) can be performed with the handheld device by using the same sound probe. For assessing Eustachian tube dysfunction, static pressure has to be generated in the sealed ear canal by means of a manometer, which has to be installed in the hand-held device. Compliance is measured while changing the pressure from +300 mm $H_2O$ pressure to 400 mm $H_2O$ pressure. Pattern recognition of the obtained tympanogram has to be performed to differentiate normal and abnormal middle ear function. For example, Eustachian tube dysfunction is indicated if maximum compliance is shifted in the negative pressure range. Also, other pathologies like otitis media with fluid filled middle ear space or otosclerosis exhibit specific tympanogram patterns, which can easily be identified by pattern recognition. In the event of the detection of abnormal middle ear function "middle ear affected", it is displayed on the screen of the handheld device. Otherwise "middle ear not affected" is indicated. In cases where no differentiation is achieved no comment is displayed.

For differentiating cochlear and neural disorders, click-evoked ABRs are recorded at high stimulus levels. By means of pattern recognition, inter-peak-latencies (IPLs) of Jewett waves I, III, and V are determined. If IPLs exceed normal ranges "auditory nerve affected" is displayed on the testing device. If IPLs are within the normal range "auditory nerve not affected" is displayed on the testing device. In cases where no differentiation is achieved, there is no comment displayed on the testing device.

Tympanometry and ABR-IPL are optional features in the handheld device of the present invention. A Flow-chart of module "Tympanometry" is shown in FIG. 6, and of module "ABR-IPL" is shown in FIG. 7.

FIGS. 9 through 13 illustrate the actual measuring sequences and possible outcomes for each measurement module, which can be selected by switches corresponding to FIG. 8.

FIG. 14 is an example of an audiogram display showing the status of measurement, status of sound probe/electrodes, comments on type and degree of auditory nerve function impairment.

An example of a preferred embodiment of the device and system is that produced by Fischer-Zoth GmbH. It is a handheld OAE and/or ABR Screening device having at least one acoustic transmitter structured for generating one or more stimuli at sound frequencies in each ear canal of a patient, which generate responsive otoacoustic emissions in both ear canals and an electric response signal on the scalp which can be detected by using ABR technique. At least one microphone is included and adapted to be removable placed in both ear canals for collecting any transient evoked and distortion product otoacoustic emissions generated by the cochlea in each ear canal in response to the stimulus to generate a frequency mixed product electronic signal. In addition, collection means, such as three electrodes placed onto the scalp, collect any click or frequency stimulated brainstem responses. A digital signal processor is associated with the microphone and electrodes to analyze their electronic signals and is programmed with signal detection algorithms and/or statistical processing instructions to evaluate acoustically stimulated signal components by means of binomial statistics or other methods to determine whether a measured signal contains stimulus elicited components for each frequency on a defined level of significance. An input device is included and associated with the microphones for inputting the frequency mixed product electronic signals and the stimulus frequencies into an incorporated computer processor. The device has an amplifier associated with a processor for elaborating the frequency mixed product electronic signals. A frequency analyzer and phase analyzer is associated with the computer processor to analyze a measured acoustic signal and separate the different frequencies and phases from one another. A display for displaying if the otoacoustic and/or the ABR signal responses are or are not statistically significant may be included. In addition the display also shows the progress and the result of the hearing threshold measurement in a form of an audiogram or other form. Also a receiver may be included for displaying on the handheld screening device all patient related date, such as infant patient's name, mother's name, birth date, address, in/outpatient, status, patient identification, hospital identification, patent history, etc. An optional modem may be included (built-in, external, or plug-in) or external network adapter then transmits the handheld OAE and/or ABR response data, such as environmental noise, probe fit, electrode impedance, signal to noise ratio, etc., to transmit data to an external data base server. An external or internal power source is associated with the computer components, microphones, transmitters, amplifiers, display means, electrodes, modem or external network adapter to operate the same.

FIG. 15 illustrates an example of audiologic measurement equipment configured as a handheld device using transiently evoked oto-acoustic emissions (TEOAE) cochlea responses to a brief click sent into the ear, DPOAE, and frequency specific ABR techniques. One combined ear probe for TEOAE/DPOAE/ABR and Tympanometry is used in conjunction with cables for the connection of the electrodes. FIG. 16 shows an ABR cable using a printout/stamp on the cable whip in order to illustrate the correct electrode connection to the user.

FIG. 17 shows how a cochlea scanning device may be used in association with audiologic testing and data inputted as a data into a PC using a NOAH database or any other database for further analysis to generate data into a HIPRO-box analysis to fit a hearing aid to the patient's needs.

Thus, the advantages of the method and apparatus of the invention allow:

Automatic non-cooperative assessment of middle ear and hair cell based hearing loss by means of extrapolated DPOAE I/O-functions. Hearing threshold is displayed in the form of a clinical audiogram. Normal hearing, slight, mild, and moderate hearing loss can be assessed with high frequency resolution. Hearing loss is classified in normal hearing, slight, mild, moderate or severe hearing loss.

Automatic non-cooperative assessment of middle ear, hair cell, and neural based hearing loss by means of extrapolated DPOAE I/O-functions and ABRs/AMFRs. Normal hearing, slight, moderate, and severe hearing losses can be assessed. Hearing threshold is displayed in the form of a clinical audiogram. Hearing loss is classified in normal hearing, slight, mild, moderate, severe or profound hearing loss.

Automatic non-cooperative adjustment of hearing aids in patients with hair cell based hearing loss by means of extrapolated DPOAE I/O-functions and ABRs/AMFRs Measurements of middle-ear impedance and ABR inter-peak-latency are conducted for the differentiation of middle-ear, cochlear, and eighth-nerve disorder. Middle-ear or eight-nerve status is assessed automatically. Comments on whether middle-ear or eighth nerve is affected or not is displayed on the audiogram form.

Hearing screening providing "pass/refer" responses.

Portable hand-held measurements, which display hearing threshold, comments on middle-ear and eight-nerve status, and classification of hearing loss. In addition, respective graphs on the screen ask the tester to insert or replace the sound probe or check the ABR/AMFR electrodes. Data are stored for adjusting hearing aids.

The invention provides a method and an apparatus to automatically and reliably assess hearing impairment without any cooperation of the subject tested, or requiring testers with extensive professional training. The results obtained represent the hearing threshold in the form of a common clinical audiogram. It is generated after inserting the sound probe in the subject's ear canal and initiating the measuring procedure. Thus, this new audiological tool fills the gap between hearing screening and audiological diagnostics for all patients, including neonates and infants. The amount of hearing loss is also classified. Depending on the amount of hearing loss, suggestions are made for further audiological testing. Additionally, hearing screening "pass/refer" responses are recorded and displayed automatically. Furthermore, the invention allows for the first time an automatic non-cooperative fitting of hearing aids in infants and adults.

The impact of undetected hearing loss to a child is long term and interferes with normal development of communication skills. Early detection of hearing loss allows early intervention, which can reduce the adverse effects of hearing impairment on speech and language development. Today, hearing screening devices only provide "pass/refer" responses. The present invention provides more detailed frequency specific and quantitative information on hearing loss in the same amount of time, with the simple handling of the apparatus, by unskilled personal. It also minimizes the necessity of subjecting newborns to conventional more thorough time-consuming investigations by audiological specialists. Thus, the application of the invention during hearing screening can also avoid the need for more thorough audiological testing in newborns and infants. The application offers a quick insight in whether and to what extent hearing capability is concerned and thus saves time and money.

Most of sensorineural hearing loss ears have a slight or moderate hearing loss. In these ears hearing impairment can be assessed with high frequency resolution by solely obtaining extrapolated DPOAE I/O-functions. Only about 0.04% of sensorineural hearing loss ears have a severe or profound hearing loss. In these cases, ABRs have to give additional information on hearing loss. In case of middle-ear pathology in most infants hearing impairment does exhibit slight hearing losses. In these ears hearing screening would yield a "fail" or "refer" response and thorough and time-consuming audiological diagnostics would normally be necessary. The invention automatically assesses hearing impairment by means of extrapolated DPOAE I/O-functions, and hearing impairment is quantitatively assessed and classified instantly. When a slight hearing loss is detected, usually no further investigation is necessary; thereby avoiding the more thorough and time-consuming conventional audiological methods. To assess moderate, severe, and profound hearing loss, the device additionally measures ABRs and/or AMFRs.

An example of the method for the assessment of sensitivity and compression of outer hair cell amplifiers by means of weighted extrapolated DPOAE I/O-functions (DPOAE Cochlea-Scan) is as follows:

According to Janssen et al. (2000) and Boege and Janssen (2002) DPOAE sound pressure I/O-functions are recorded in a wide primary tone level range (e.g. −10 dB<L2<70 DBSPL, L1=0.4L2+39, f2/f1=1.2). Due to the linear dependency of the DPOAE sound pressure on the primary tone sound pressure level DPOAE sound pressure I/O-functions can be described by the two parameters a and b of the linear fit:

$$p_{DP}(L_2)=a \cdot (L_2-b)$$

Parameter a gives the slope s of the linear DPOAE sound pressure I/O-function, which is constant over $L_2$ in contrast to the varying slope of the DPOAE sound pressure level I/O-function (compare upper and lower panel in FIG. 1a). The second parameter b represents the value for $L_2$ where DPOAE pressure is zero (point of intersection between extrapolated and is named as $L_{EDPT}$. Thus, $$P_{DP}(L_2)=s \cdot (L_2-L_{EDPT}),$$

with $L_2=20$ dB·log ($p_2/20$ μPa) and the two fit parameters, threshold $$L_{EDPT}=20 \text{ dB·log } (b/20 \text{ μPa})$$

and slope $$s=(a/20) \text{ μPa/dB}.$$

According to Oswald et al. (2002) weighted Least Mean Square Extrapolation for fitting the DPOAE sound pressure I/O-function is applied:

$$\text{Min}[\Sigma w_1 w_2 (p_{DP}(L_2)-p(L_2))^2] \text{ with } w_1=70-L_2 \text{ and } w_2=\text{SNR}(L_2)/6 \text{ dB}$$

where $w_1$ is the factor which is weighting close-to-threshold DPOAEs higher and $w_2$ is the factor which is weighting DPOAEs with high signal-to-noise ratios higher. The difference in predicting $L_{EDPT}$ is shown in FIG. 1b, where DPOAE data (circles) are fitted by unweighted and weighted LMSE. In FIG. 1 b L2th means $L_{EDPT}$.

The point of intersection of the weighted extrapolated DPOAE sound pressure I/O-function $L_{EDPT}=20$ dB·log (b/20 μPa) and the L2 axis provides the objective measure for assessing loss of sensitivity (hearing loss). The slope of the weighted DPOAE sound pressure I/O-function s=(a/20) μPa/dB provides an objective measure for assessing loss of compression. After conversion from sound pressure level (SPL) to hearing loss (HL), the $L_{EDPT}(f_2)$ value which is calculated for the selected f2 frequencies is inserted in the audiogram form giving the hearing threshold (respectively hearing loss) of the subject tested.

DPOAE I/O-functions are recorded not only at frequencies used in conventional audiograms but are also obtained between these frequencies. The advantage of high-frequency resolution scanning of cochlear dysfunction is twofold. First, hearing loss can be predicted in a wider range. For example, in a cochlear hearing loss ear having a steep high frequency hearing loss at 4 kHz DPOAEs may not be measured at 6 kHz due to severe hearing loss but at a frequency slightly below 6 kHz where the hearing loss is lower. In this case the hearing loss at 6 kHz can be estimated by means of extrapolating the obtained hearing threshold values at f2 frequencies below 6 kHz. Thus, hearing threshold can be constructed and displayed including the 6 kHz audiogram frequencies.

Second, when interpolating, the obtained hearing threshold values within the complete frequency range contribution of outer hair cell amplifiers from cochlea sites well below and above the audiogram frequencies can be additionally considered. Thus, an assessment of narrow-band cochlear dysfunction is possible. In view of fitting multi-channel hearing aids, the average of hearing threshold and compression values within the respective bandwidth of the channel may provide more suited fitting parameters.

In addition, the audiogram form contains areas indicating normal hearing, slight, mild, moderate, severe, and profound hearing loss (see FIG. 14). Depending on maximum hearing loss the corresponding area is marked (e.g. high-lighted) and thus provides a comment on the degree of hearing loss in addition to hearing threshold.

An example of how the method works for Automatic non-cooperative hearing aid fitting (ANC-Hearing Aid Fitting) by providing hearing aid fitting parameters on the basis of the assessment of sensitivity and compression of outer hair cell amplifiers by means of extrapolated DPOAE I/O-functions (DPOAE Cochlea-Scan) is as follows:

DPOAE I/O-functions are measured at selected frequencies. An example for a DPOAE I/O-function of an impaired ear for a selected frequency is presented in FIG. 4. At the right hand side of FIG. 4 the patient's extrapolated DPOAE I/O-function (solid line) and that of normally hearing subjects (mean is represented by dashed line, standard deviation by shaded area) are shown for frequency f2=2002. Triangle symbols indicate noise floor. Due to the noise, the patient's DPOAEs (filled circles) could be measured only down to 45 dB. The difference between normal and impaired DPOAE I/O-function indicates loss of sensitivity and compression of the outer hair cell amplifiers at the patient's f2 cochlea place. At the left hand side of FIG. 4 the patient's extrapolated DPOAE I/O-function (tested ear) is plotted against the primary tone level of normative data (L2-Norm). The intersection of the arrow with the L2-axis provides the patient's hearing loss. The horizontal bars provide the gain of hearing aid needed to yield patient's normal hearing at different input levels at tested frequency. For example, sound of a sound pressure level of 50 dB has to be amplified by 30 dB, sound of a sound pressure level of 60 dB has to be amplified by 20 dB, sound of a sound pressure level of 70 dB has to be amplified by 10 dB, and sound of a sound pressure level of 80 dB has to be amplified by only 3 dB to reach normal hearing. It has to be emphasized, that due to extrapolation, calculation of needed gain is not only possible for close to threshold sound intensities but also for sound intensities above the border of DPOAE measurement. Thus, the needed gain for normal hearing can be calculated with the presented method for any sound to be amplified by the hearing aid. Today, due to artificial distortion of the receivers of the sound probe, DPOAE measurement is restricted to a primary tone sound pressure level of about 70 dB SPL.

The calculated hearing aid fitting parameters have to be obtained at different f2 frequencies corresponding to the frequencies of hearing aid channels. A hearing aid specific computer software (e.g. running under NOAH) may be used to interpret the measurements and prepare data to adjust the hearing aid via an interface (e.g. HI-PRO) (see flow chart in FIG. 5).

Sound pressure at the eardrum may be calculated for selected frequencies from the estimated individual ear canal length and volume. By determining sound pressure maxima in the frequency response, middle ear/inner ear impedance is measured or estimated (e.g. by using models) in order to control the loudspeakers' voltage for generating defined sound pressure in the front of the eardrum.

Additional acoustic stimuli (e.g. noise of suited bandwidth or sinusoidals) may be delivered in the outer ear canal in order to suppress secondary responses generated below and above the cochlea site of the primary response. In addition to the recording of OAE and ABR I/O-functions, ABR-Inter-Peak-Latency assessment and tympanometry for differentiating middle-ear, cochlear and neural disorders may be performed.

Generally, the electrodes' impedance is measured and in the event of sufficient conductivity (user defined) measuring is continued automatically. If it is insufficient, the tester is directed to check the electrodes.

Additional features of the method and the invention are discussed below.

DESCRIPTION OF THE DRAWINGS

FIG. 4 is an example of how to derive hearing aid fitting parameters from extrapolated DPOAE I/O-functions.

FIG. 16 is a schematic of associated hardware components.

DESCRIPTION OF THE ILLUSTRATED EMBODIMENTS

Figure 1:
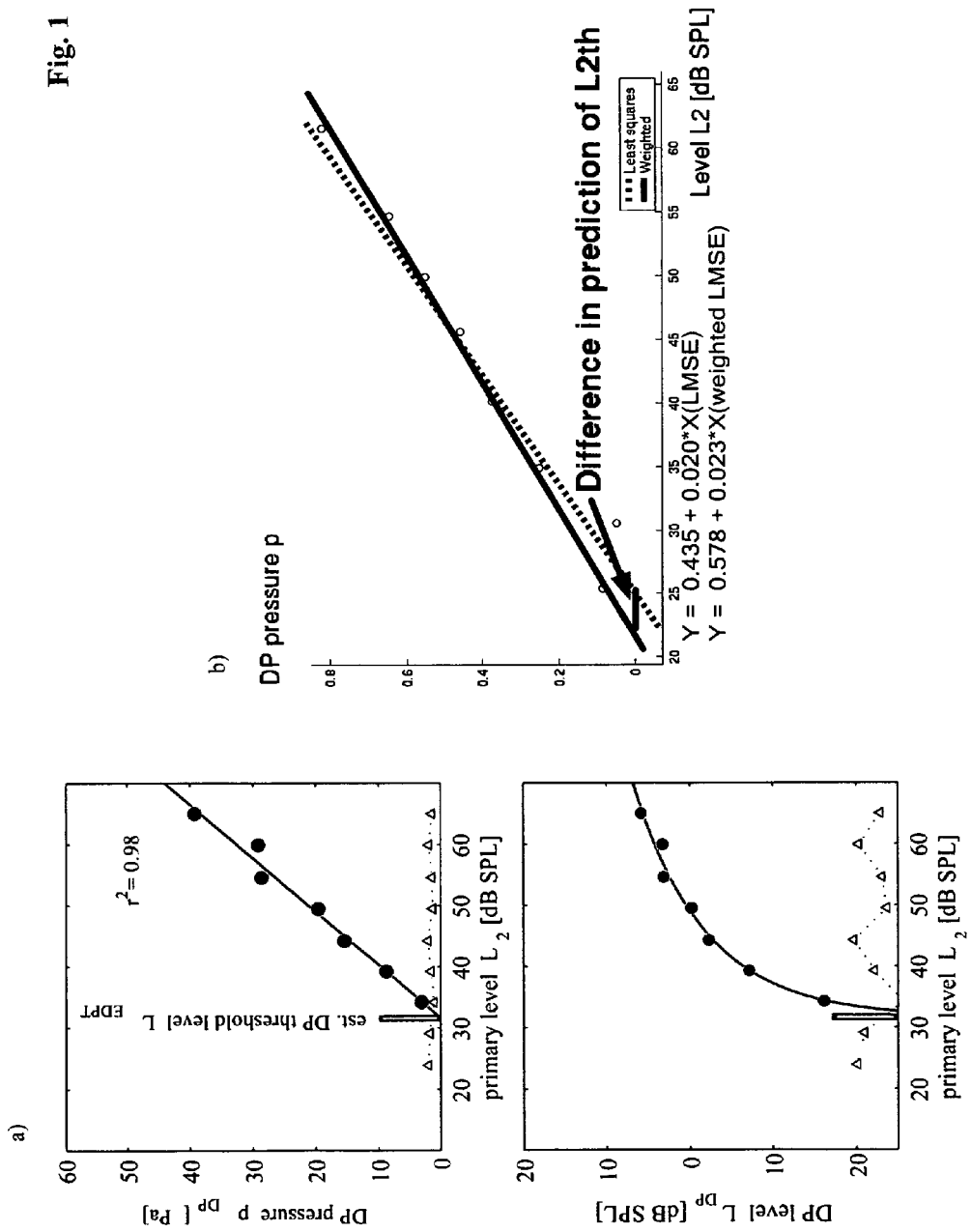
FIG. 1a is a plot of DPOAE sound pressure (top) and the DPOAE sound pressure level (bottom) as a function of the primary tone level.
FIG. 1b is a plot of extrapolated DPOAE I/O-function using simple regression analysis and weighted regression analysis and showing differences in predicting the level at DPOAE threshold (L2th).

FIG. 1a is a plot of the DPOAE sound pressure $p_{DP}$ (upper panel) and the DPOAE sound pressure level $L_{DP}$ (lower panel) of the same DPOAE I/O-function as a function of the primary tone level $L_2$. The linear fit to the data (solid line) proves the logarithmic dependency of $p_{DP}$ on $p_2$.

Figure 2:
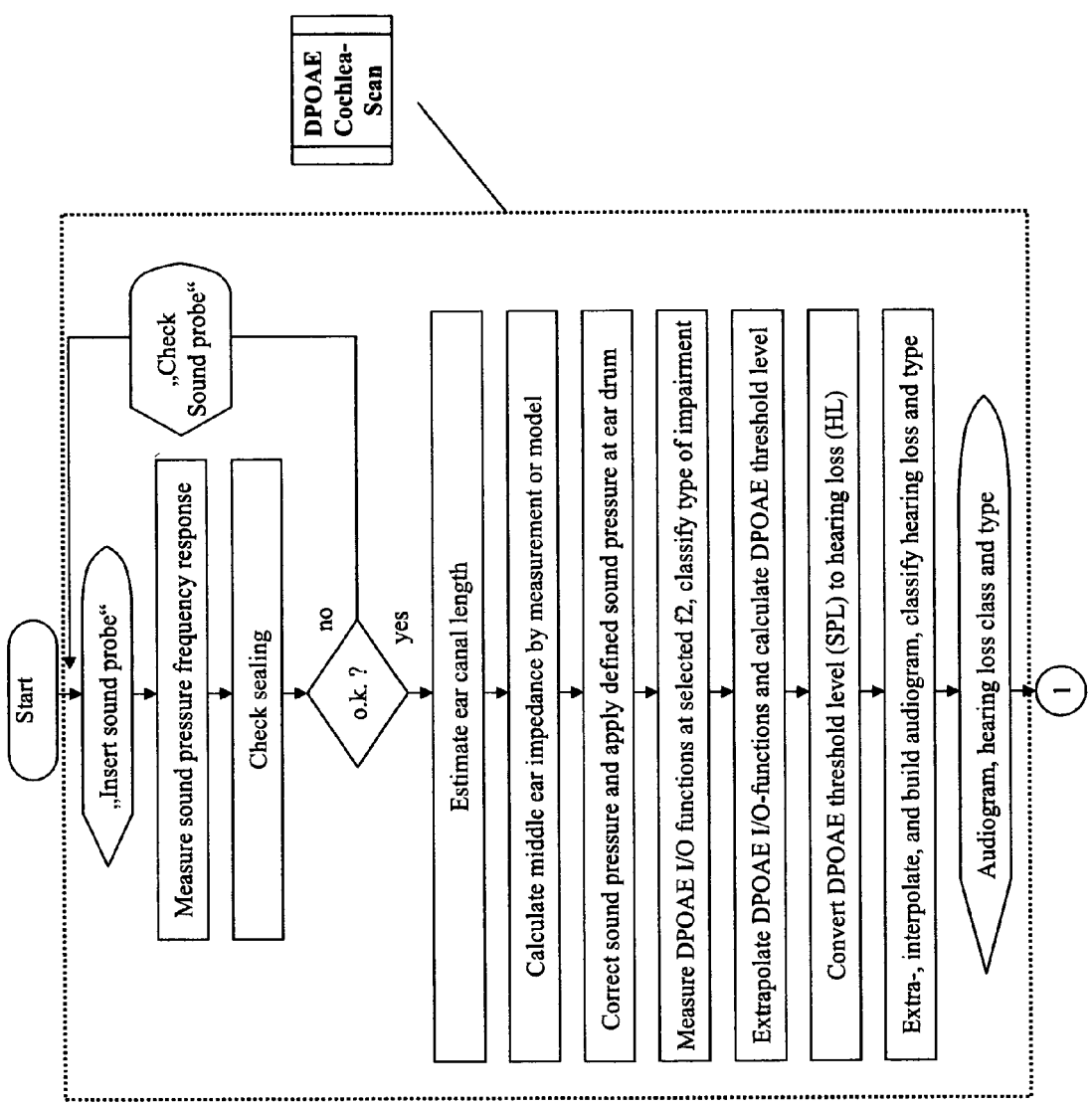
FIG. 2 is a schematic of DPOAE Cochlea-Scan measurement.

FIG. 2 is a schematic of DPOAE Cochlea-Scan measurement.

Figure 3:
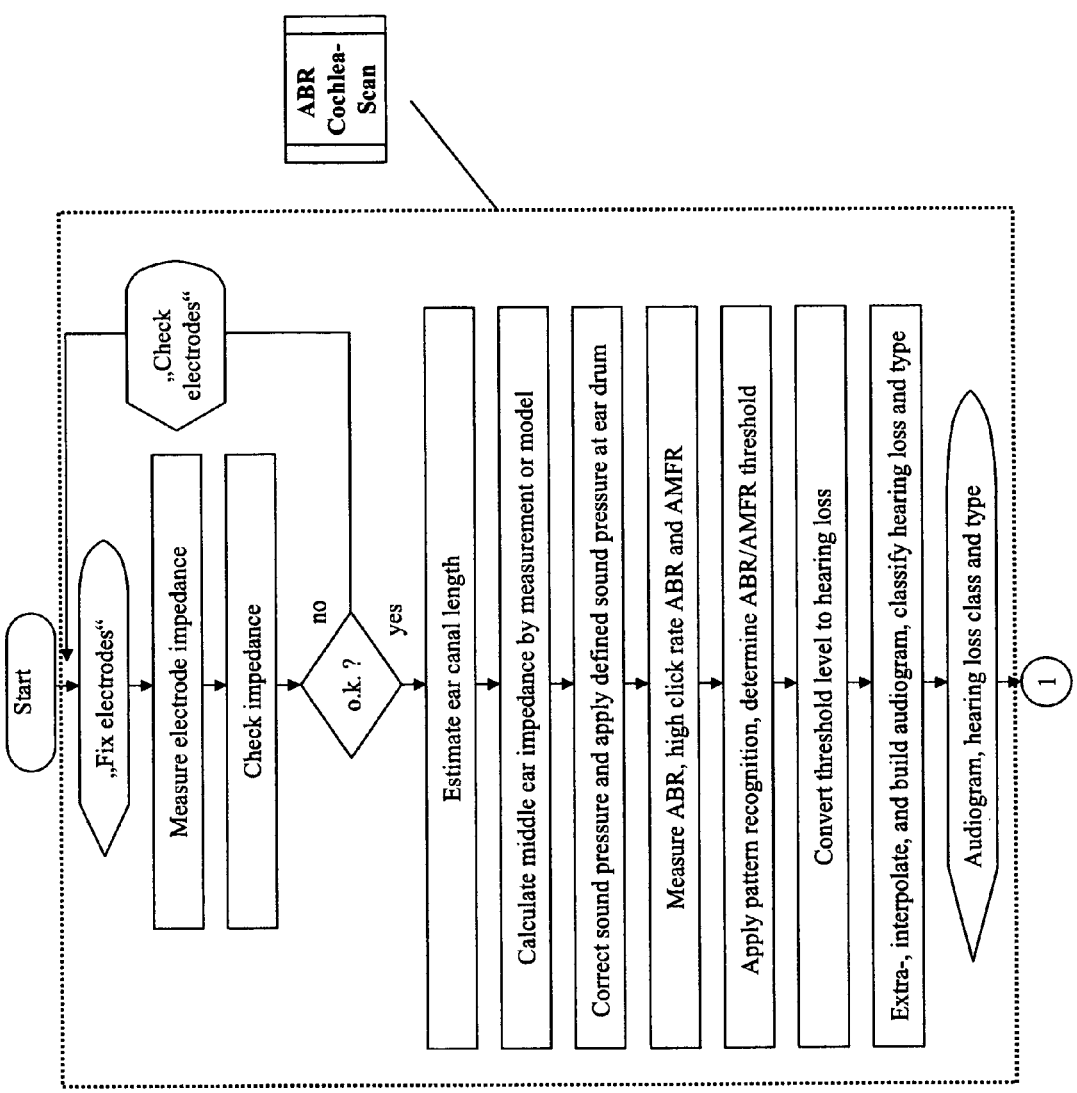
FIG. 3 is a schematic of a preferred ABR Cochlea-Scan measurement sequence.

FIG. 3 is a schematic of ABR Cochlea-Scan measurement.

FIG. 4 is an example of how to derive hearing aid fitting parameters from extrapolated DPOAE I/O-functions.

Figure 5:
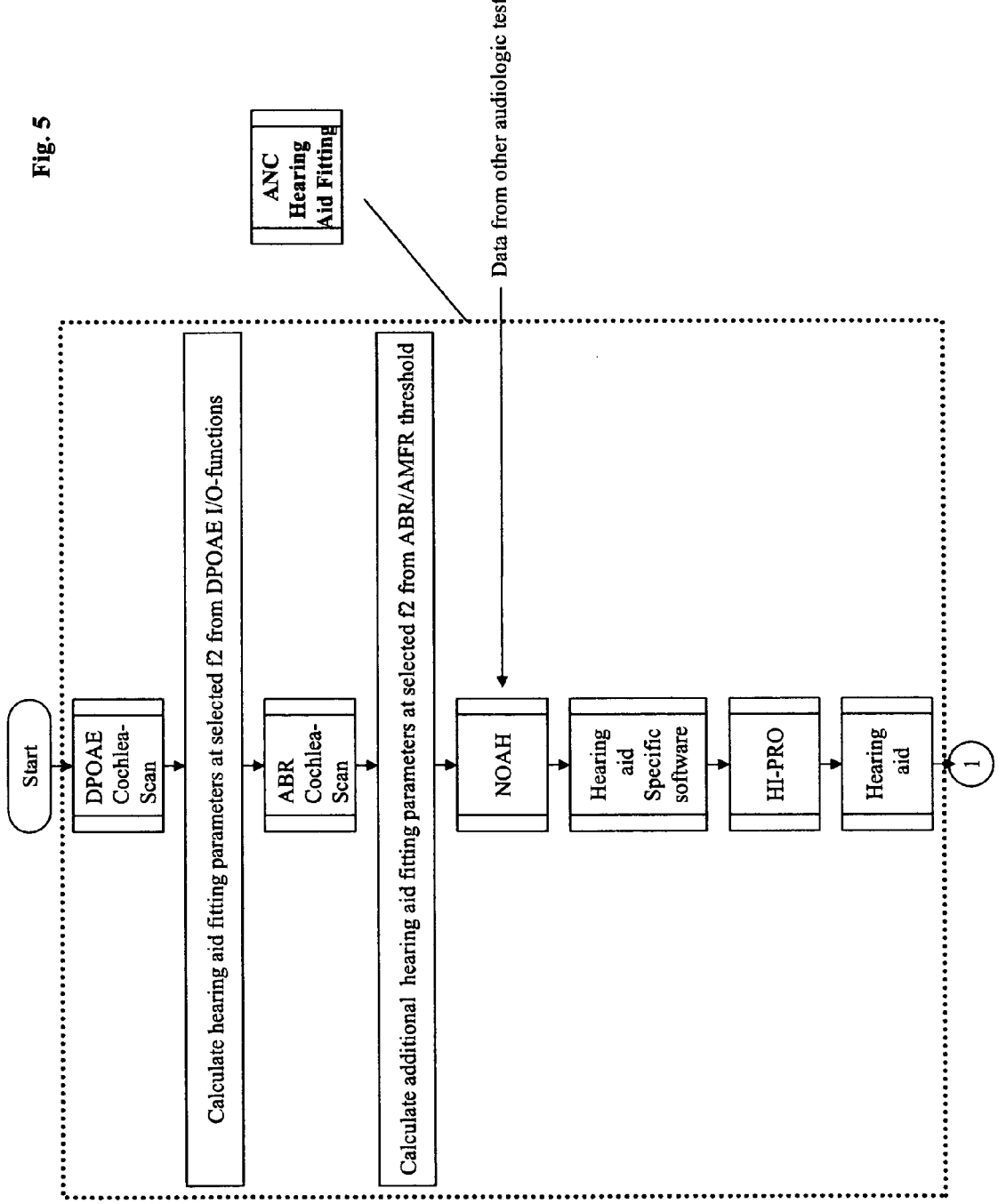
FIG. 5 is a schematic of how to manage automatic non-cooperative hearing aid fitting.

FIG. 5 is a schematic of how to manage automatic non-cooperative hearing aid fitting.

Figure 6:
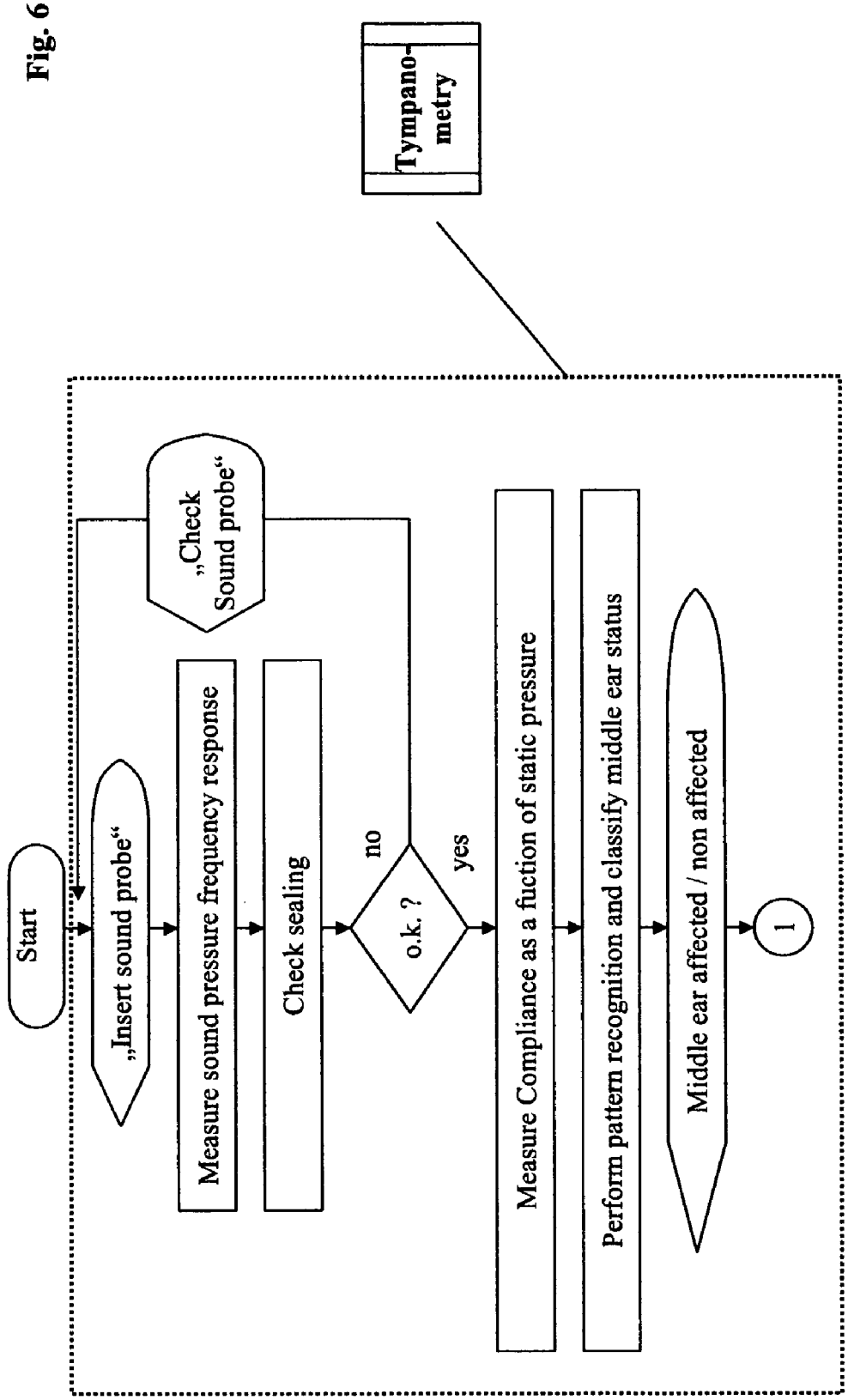
FIG. 6 is a schematic of tympanometry for automatically assessing middle ear status.

FIG. 6 is a schematic of tympanometry for automatically assessing middle ear status.

Figure 7:
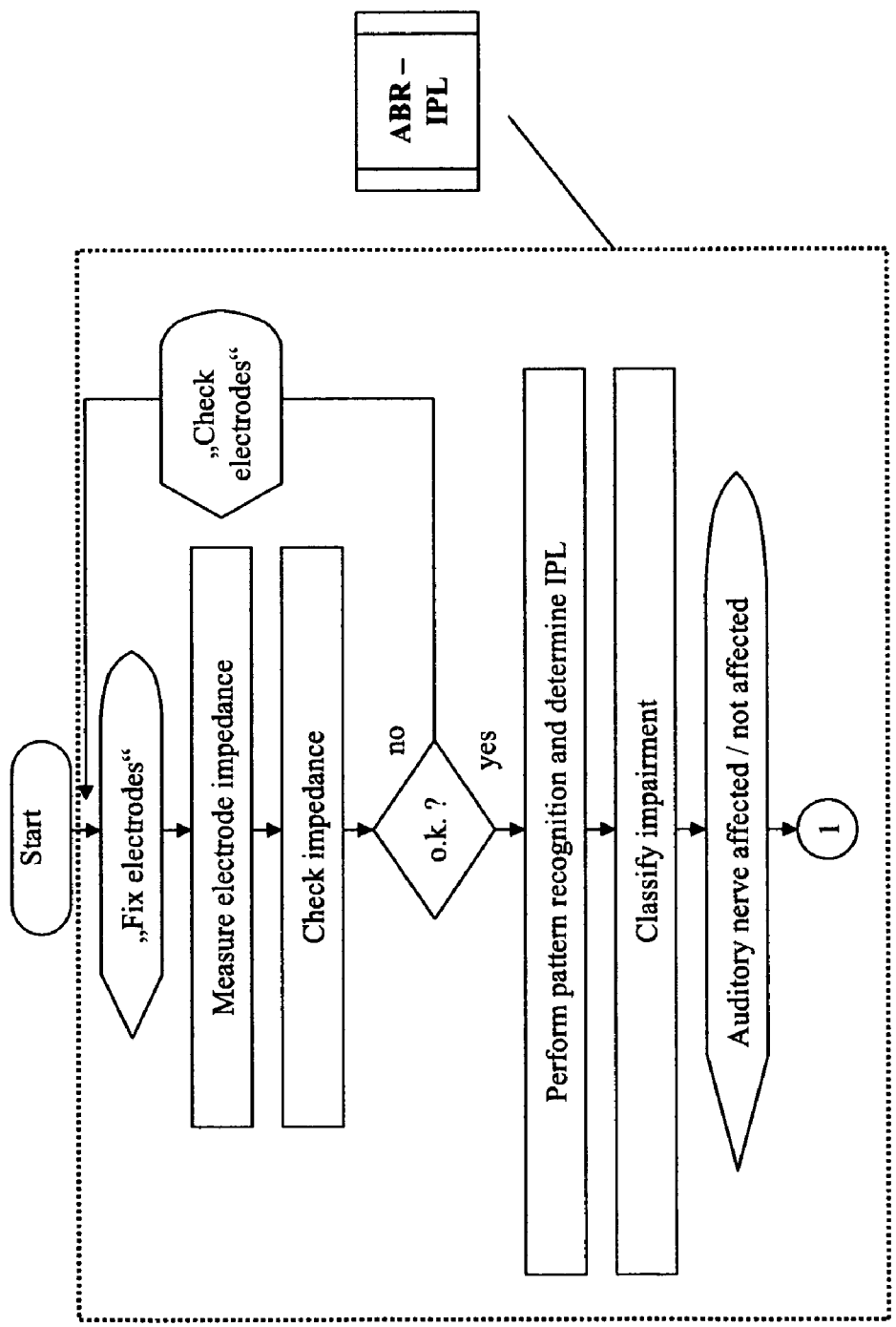
FIG. 7 is a schematic of ABR Inter-Peak-Latency for automatically assessing eighth (auditory) nerve disorder.

FIG. 7 is a schematic of ABR Inter-Peak-Latency for automatically assessing eighth (auditory) nerve disorder.

Figure 8:
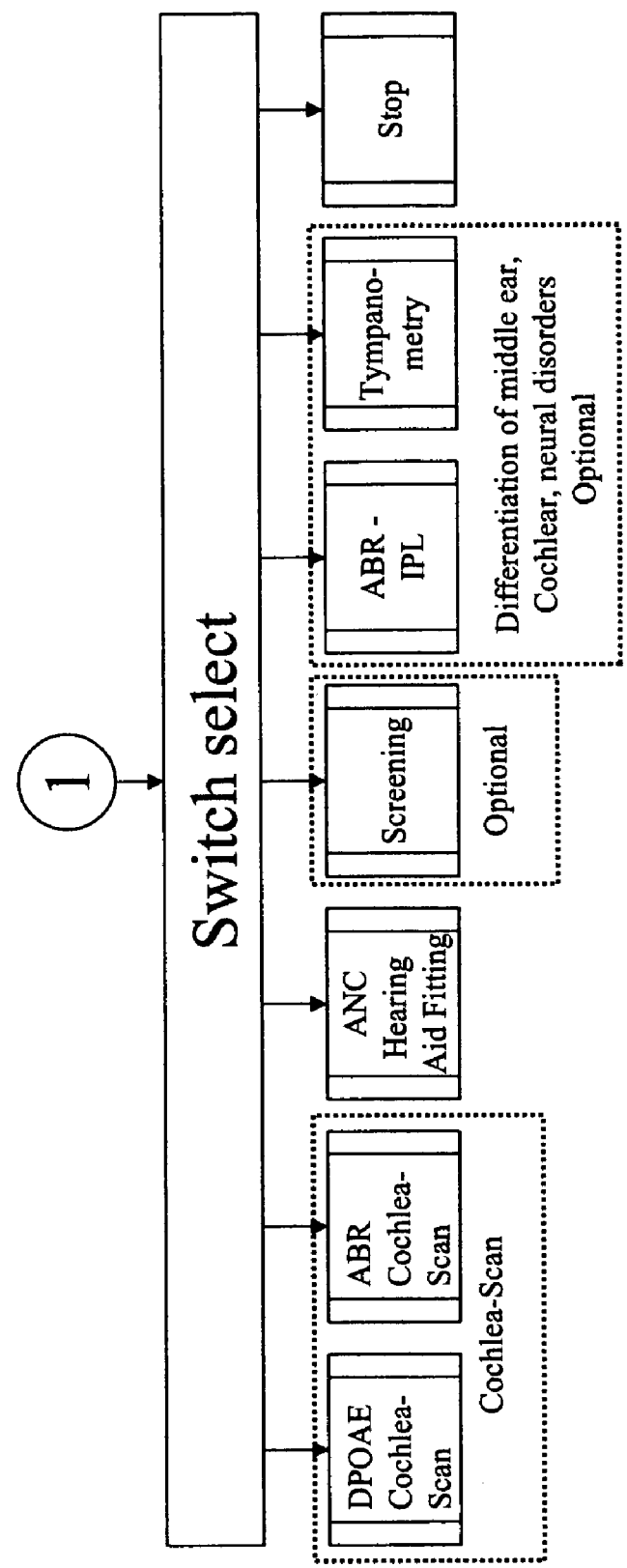
FIG. 8 is a schematic of the switch selector.

FIG. 8 is a schematic of a switch selector used to active the scanning device. Initially, an operator selects either a DPOAE and/or an ABR cochlea scan to active the microphone multiple range sound signal generator and the responses are collected displayed on a display screen or printed out via a printer (not shown). These signal responses are then separately analyzed by selecting the Screening, ABR IPL, and Tympanometry features, which selectively gather the related input data from the various system components described above. Lastly, the hearing aid fitting switch is activated to display the recommended hearing aid fitting based on the analyzed signal responses and to prepare data to adjust the hearing aid via an interface.

Figure 9:
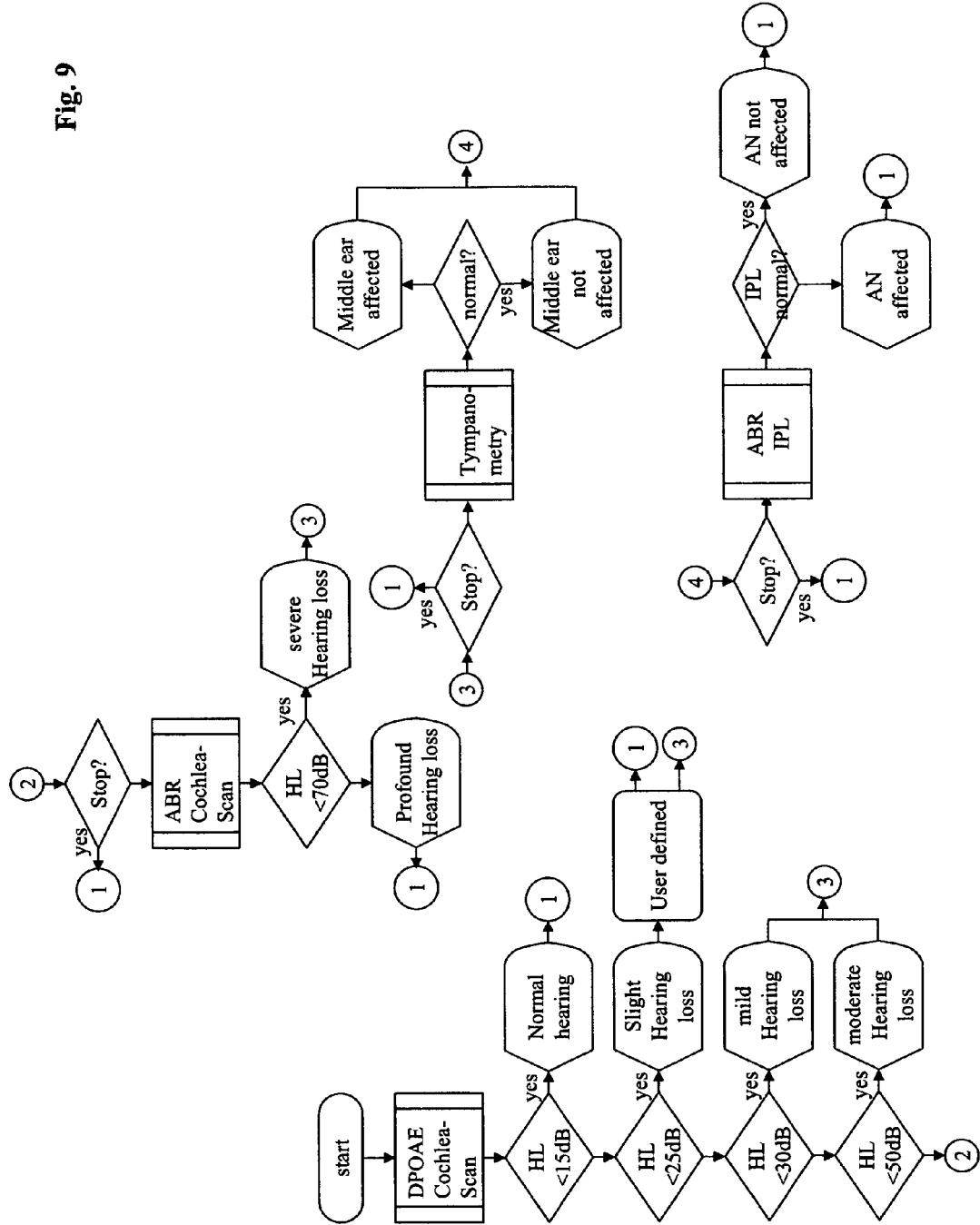
FIGS. 9 through 13 are schematics of the key activated automatic testing sequences of the switch selector.

FIGS. 9 through 13 illustrate preferred actual measuring sequences and possible outcomes for each switch selected in FIG. 8. The device employs DPOAE Cochlea-Scan measurement in the event of estimated hearing loss being lower than e.g. 15 dB for all frequencies indicates "normal hearing." In the event estimated hearing loss is more than e.g. 15 dB HL and lower than 25 dB HL for at least one frequency, it indicates "slight hearing loss." In the event estimated hearing loss is more than e.g. 25 dB HL and lower than 30 dB HL for at least one frequency, it indicates "mild hearing loss." In the event of estimated hearing loss being more than e.g. 30 dB HL and lower than 50 dB HL for at least one frequency, it indicates "moderate hearing loss." And, in the event of estimated hearing loss more than 50 dB HL for at least one frequency, it indicates "severe hearing loss" or profound hearing loss depending on ABR Cochlea Scan as shown in FIG. 9. Respective audiograms and comments are displayed on the screen to reflect these findings.

Figure 10:
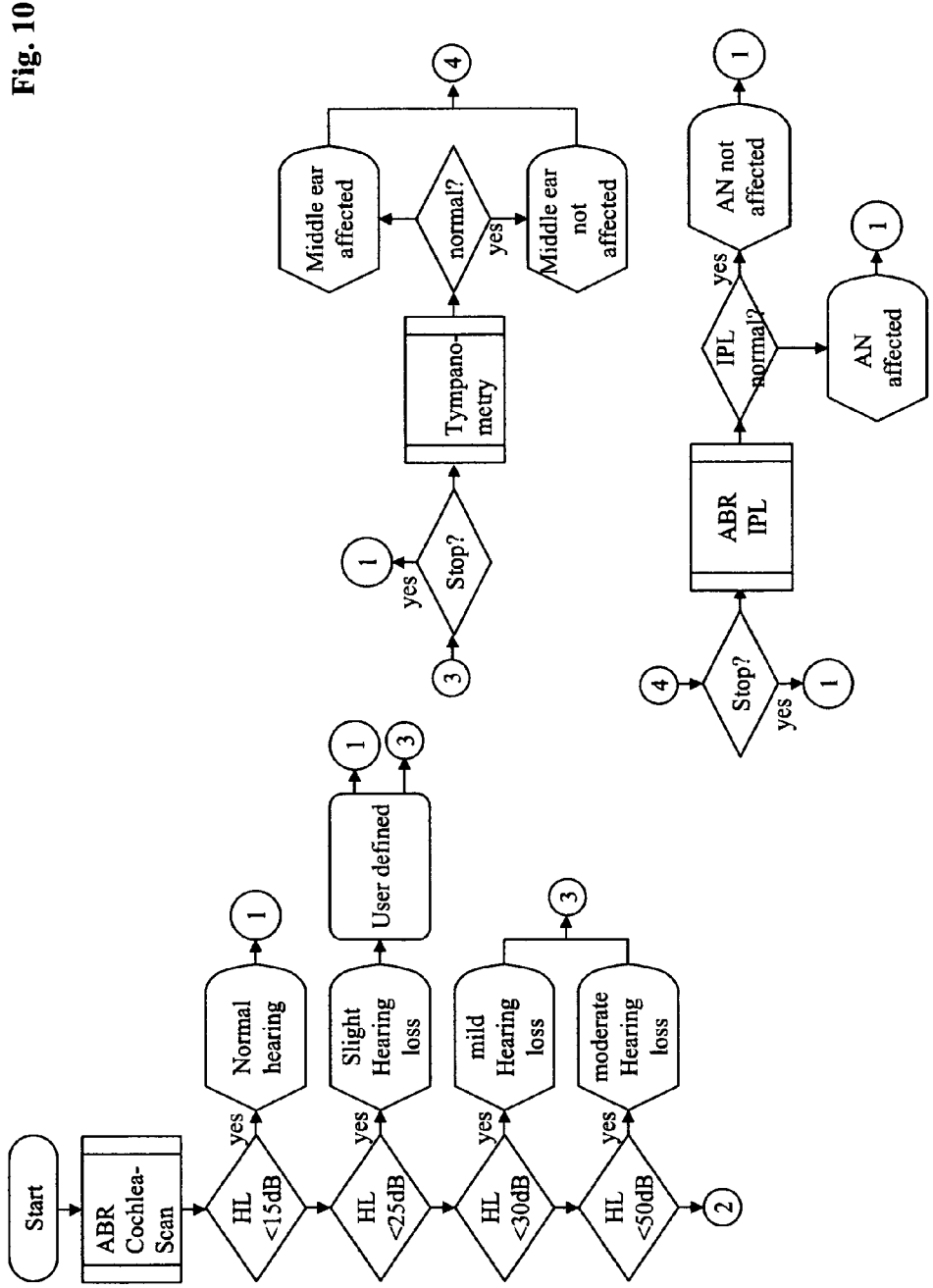

FIG. 10 illustrates the remaining testing sequences in the event of each hearing outcome.

For "normal hearing," the switch "stop" sequence is initiated. For "slight hearing loss", a user defined sequence is initiated wherein either the "stop" sequence is initiated, or a tympanometry testing sequence is performed. If the tympanometry results show "normal", a "middle ear not affected" display is shown and the switch "stop" sequence is initiated or an ABR IPL testing sequence is performed. If the tympanometry results are not "normal", a "Middle ear affected" display is shown and the "stop" sequence is initiated or the ABR IPL testing sequence is performed.

The ABR IPL sequence first tests IPL. If the IPL is normal, an "AN not affected" is displayed and the switch "stop" sequence is initiated. If the IPL is not normal, a display "AN affected" is displayed.

Figure 11:
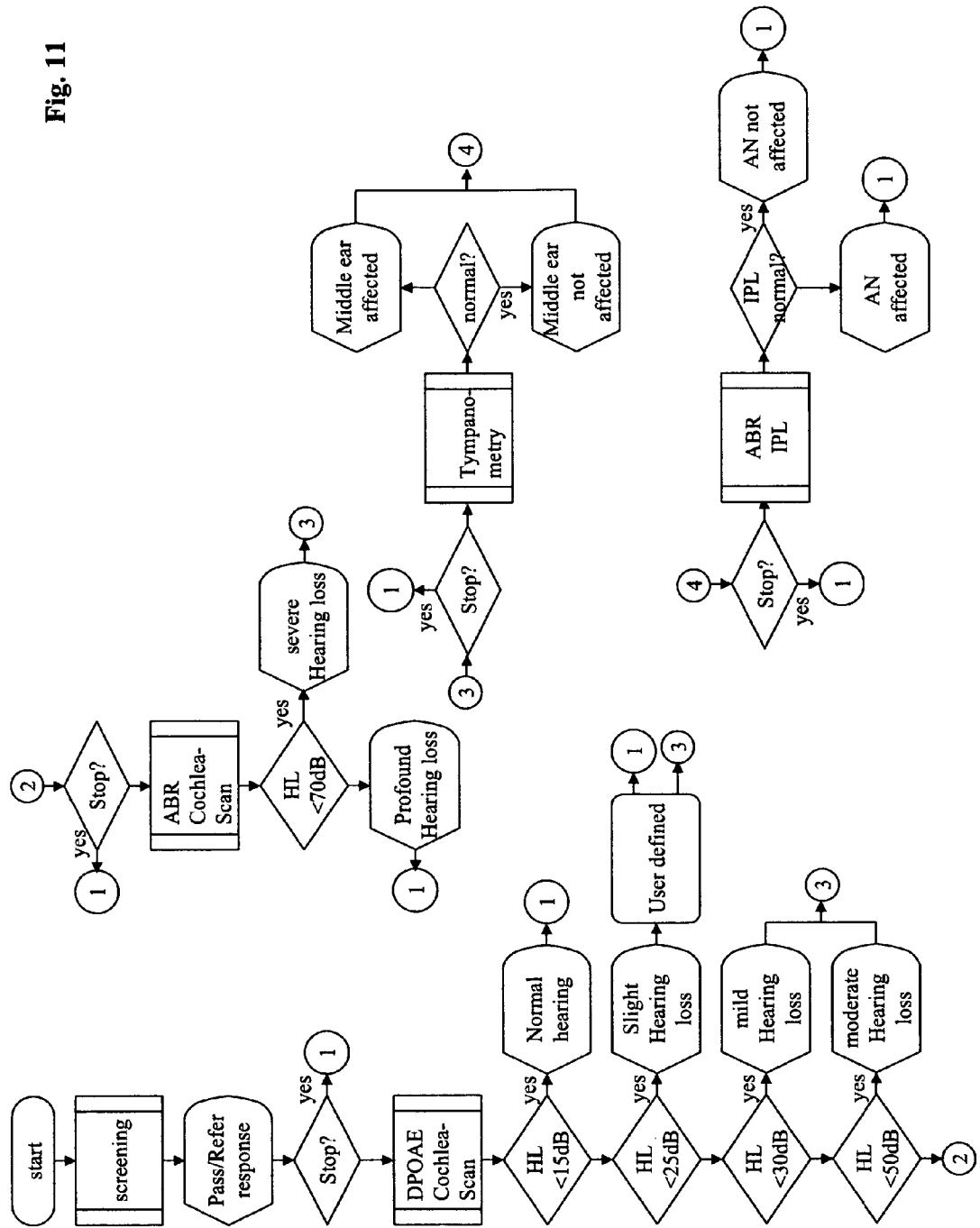
Figure 12:
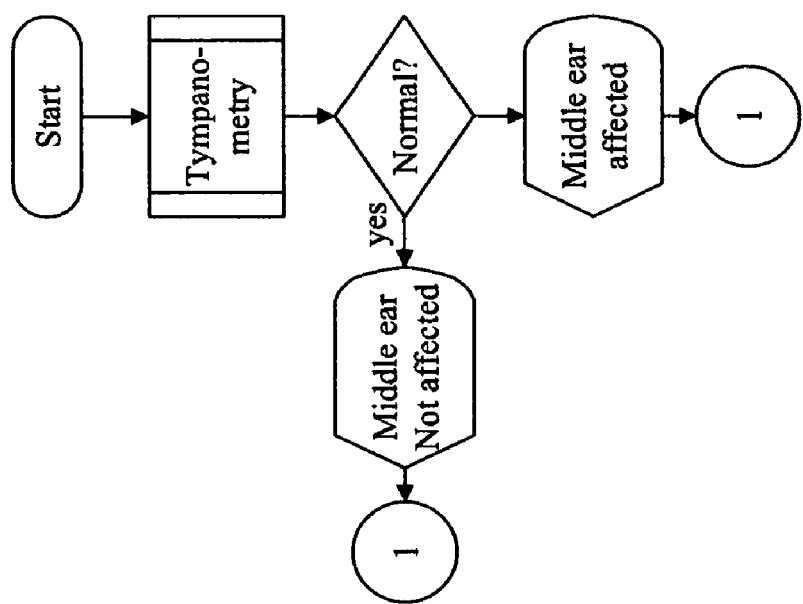
Figure 13:
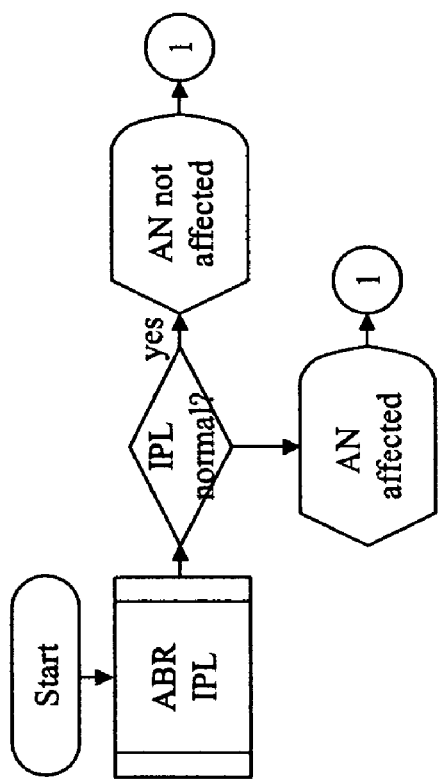

FIG. 11 indicates the testing sequence for hearing loss in excess of 50 decibels. An ABR Cochlea-Scan is performed. If it shows a hearing loss less than 70 decibels, then a "Profound Hearing Loss" display is indicated, and the "stop switch" sequence is displayed. If the hearing loss is greater than 70 dB, a "Severe Hearing Loss" display is indicated and the Tympanometry measuring sequence may then be instigated or the stop switch activated. If the Tympanometry is not normal, the "Middle Ear Affected" display is indicated. If the Tympanometry is normal, the "Middle Ear Not Affected" display is shown. For both "Middle Ear Affected" and "Middle Ear Not Affected" results, ABR IPL testing is then conducted. If the tympanometry results are not "normal", a "Middle ear affected" display is shown and the "stop" sequence is initiated or the ABR IPL testing sequence is performed. This ABR IPL sequence then tests IPL, and if the IPL is normal, an "AN not affected" is displayed and the switch "stop" sequence is initiated. If the IPL is not normal, a display "AN affected" is displayed.

Figure 14:
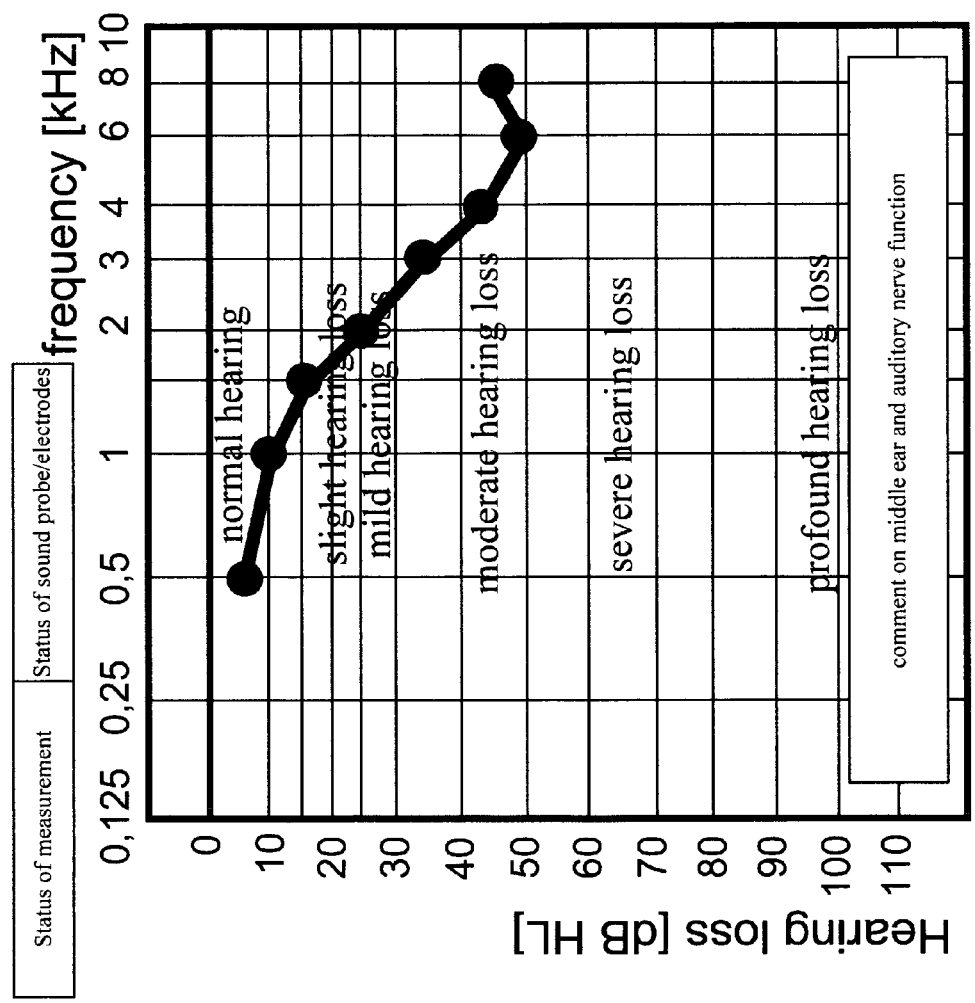
FIG. 14 illustrates how hearing threshold and classification of hearing loss is displayed on the screen of the handheld device.

FIG. 14 is an audiogram display. The hearing loss (dBHL) is plotted against frequency (kHz) with the thick black line showing a patient's hearing threshold at each respective frequency. Depending on the degree of hearing loss for example moderate hearing loss the respective area is highlighted. Additionally, the type of hearing impairment as far as it could be determined as well as status of measurement and status of sound probe/electrodes are displayed. Preferably, computer pattern recognition classifies tympanograms and displays their status as:

For a peaked tympanogram with normal compliance, it indicates normal middle-ear function.

For a peaked tympanogram with low compliance, it indicates otosclerosis.

For a flat tympanogram with low compliance, it indicates a fluid filled tympanic cavity, For a tympanogram with maximum compliance shifted in the negative pressure range, it indicates Eustachian tube dysfunction.

A typical display screen is included and shows "auditory nerve affected" or "auditory nerve not affected", "Eustachian tube dysfunction". etc. in response to the above measurements.

Figure 15:
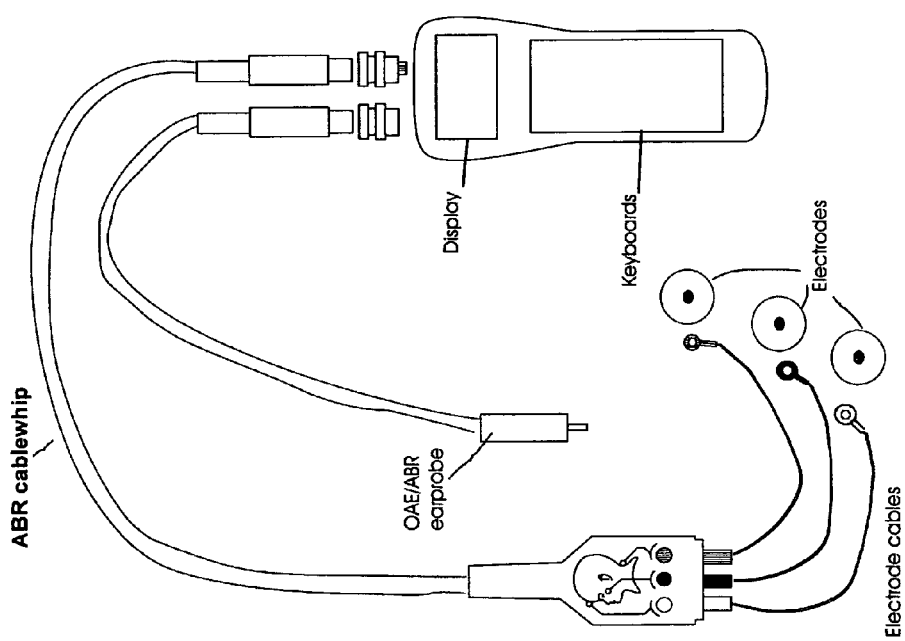
FIG. 15 is a schematic showing a cochlea scanning device may be used in association with audiologic testing

FIG. 15 illustrates an example of preferred audiologic measurement equipment configured as a handheld device using TEOAE, DPOAE, and frequency specific ABR technique, one combined ear probe for TEOAE/DPOAE/ABR and Tympanometry is used in conjunction with cables for the connection of the electrodes.

Figure 17:
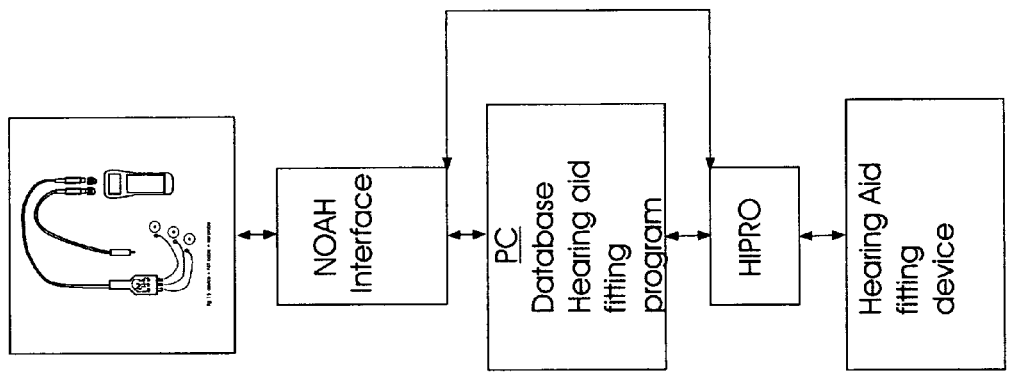
FIG. 17 is a schematic showing a cochlea scanning device used in association with audiologic testing and data inputted as a data into a PC for further analysis to generate data into a HIPRO-box analysis to fit a hearing aid to the patient's needs.

FIG. 16 shows a detail of the ABR cable connection FIG. 17 is a schematic showing how the cochlea scanning device may be used in association with audiologic testing data inputted as a data into a PC for further analysis to generate data into a HIPRO-box analysis to fit a hearing aid to the patient's needs.

Although this specification has referred to the illustrated embodiments, it is not intended to restrict the scope of the appended claims. The claims themselves recite those restrictions deemed essential to the invention.

We claim:

1. A method for automatically assessing loss of hearing sensitivity and loss of compression with user defined frequency resolution by means of extrapolated Otoacoustic Emission Input/Output functions (OAE I/O-functions) and Auditory Brain Stem Responses (ABRs) as well as for automatically fitting hearing aids comprising: generating one or more acoustic stimuli in the subject's ear canal by means of a sound probe, wherein the sound probe further comprises a sound probe seal, and an acoustic stimuli generator, recording any Transient Evoked Otoacoustic Emissions (TEOAEs) and Distortion Product Otoacoustic Emissions (DPOAEs) generated by the cochlea in the subject's ear canal in response to the acoustic stimuli by collector means, inputting the collector means' output-signal into a signal processor, calibrating the acoustic stimuli in the ear canal by checking the sound probe's seal and estimating sound pressure proximate the eardrum by generating a defined stimulus level signal in front of the eardrum, analysing amplitude, phase, and frequency of cochlear responses, evaluating the responses and signals by binominal statistics or signal-to-noise estimates to determine whether the measured signals contain stimulus correlated components on a defined level of significance, estimating the cochlear responses at threshold as well as at stimulus levels higher than applied by extrapolating cochlear responses that are generated within the dynamic range of the acoustic stimulation, converting the estimated stimulus levels at threshold into hearing loss levels and reconstructing a clinical audiogram for display, and estimating cochlear compression from extrapolated OAE I/O-functions for providing the gain of hearing aid needed to provide subject's normal hearing.

2. A method for automatically assessing loss of hearing sensitivity and loss of compression with user defined frequency resolution by means of extrapolated OAE I/O-functions and ABRs as well as for automatically fitting hearing aids according to claim 1, including:
   a. expanding the assessment of hearing loss and loss of compression by additionally measuring to the stimuli,
   b. providing objective hearing aid fitting parameters derived from estimated hearing loss and compression testing data, analysing the data using hearing aid specific software, and adjusting the hearing aid via an interface,
   c. measuring middle-ear impedance for checking middle ear status,
   d. measuring ABR inter-peak-latency for checking eighth-nerve function,
   e. performing newborn hearing screening providing "pass/refer" responses,
   f. accelerating measurement by automatically intervening in the measuring process by querying the status of different measuring procedures and values, and
   g. indicating type and degree of hearing loss by displaying respective graphs and comments.

3. A method for automatically assessing loss of hearing sensitivity and loss of compression with user defined frequency resolution by means of extrapolated OAE I/O-functions and ABRs as well as for automatically fitting hearing aids according to claim 2, including measuring high click rate evoked ABRs and/or AMFRs if the calculation of hearing loss and compression loss by means of OAE I/O-functions is incomplete.

4. A method for automatically assessing loss of hearing sensitivity and loss of compression with user defined frequency resolution by means of extrapolated OAE I/O-functions and ABRs as well as for automatically fitting hearing aids according to claim 3, wherein high click rate evoked ABRs and/or AMFRs are calculated from the frequency spectrum providing I/O-functions for estimating threshold and compression of cochlear responses and are used for providing hearing aid fitting parameters especially in that range where OAE threshold and compression estimates are missing.

5. A method for automatically assessing loss of hearing sensitivity and loss of compression with user defined frequency resolution by means of extrapolated OAE I/O-functions and ABRs as well as for automatically fitting hearing aids according to claim 4, including employing threshold estimates for reconstructing the clinical audiogram where OAE threshold estimates are missing.

6. A method for automatically assessing loss of hearing sensitivity and loss of compression with user defined frequency resolution by means of extrapolated OAE I/O-functions and ABRs as well as for automatically fitting hearing aids according to claim 2, including using OAE/ABR threshold and compression estimates for calculating hearing aid fitting parameters and adjusting the hearing aid for compensating loss of sensitivity and loss of compression in its different channels.

7. A method for automatically assessing loss of hearing sensitivity and loss of compression with user defined frequency resolution by means of extrapolated OAE I/O-functions and ABRs as well as for automatically fitting hearing aids according to claim 6, including calculating hearing threshold level and input-level dependent gain from extrapolated DPOAE I/O-functions, and calculating and preparing hearing aid fitting parameters by using hearing aid specific computer software to generate hearing aid fitting parameters also used to adjust the hearing aid.

8. A method for automatically assessing loss of hearing sensitivity and loss of compression with user defined frequency resolution by means of extrapolated OAE I/O-functions and ABRs as well as for automatically fitting hearing aids according to claim 7, including calculating hearing threshold level and input-level dependent gain from extrapolated ABR, and/or AMFR I/O-functions and/or calculating them from I/O functions reconstructed from a mixture of OAE, ABR, and AMFR functions that are reconstructed of a mixture of OAE, ABR, and AMFR I/O-functions using hearing aid specific computer software to generate hearing aid fitting parameters also used to adjust the hearing aid.

9. A method for automatically assessing loss of hearing sensitivity and loss of compression with user defined frequency resolution by means of extrapolated OAE I/O-functions and ABRs as well as for automatically fitting hearing aids according to claim 2, including performing ABR-Inter-Peak-Latency assessment and tympanometry for differentiating middle-ear, cochlear, and neural disorders.

10. A method for automatically assessing loss of hearing sensitivity and loss of compression with user defined frequency resolution by means of extrapolated OAE I/O-functions and ABRs as well as for automatically fitting hearing aids according to claim 2, including measuring electrode impedance and in the an event of sufficient user defined conductivity, continuing measuring automatically, or, if insufficient, directing a tester to check a plurality of electrodes.

11. A method for automatically assessing loss of hearing sensitivity and loss of compression with user defined frequency resolution by means of extrapolated OAE I/O-functions and ABRs as well as for automatically fitting hearing aids according to claim 2, including determining by means of pattern recognition ABR Inter-Peak-Latencies (IPLs), and displaying the following respective comments:
 a. if normal IPLs, auditory nerve not affected,
 b. if IPLs exceed normal ranges, auditory nerve is affected, and
 c. if no IPL determination is possible, no comment.

12. A method for automatically assessing loss of hearing sensitivity and loss of compression with user defined frequency resolution by means of extrapolated OAE I/O-functions and ABRs as well as for automatically fitting hearing aids according to claim 2, including analysing and classifying tympanogram patterns for display as follows:
 a. for a peaked tympanogram with normal compliance, an indicator as normal middle-ear function,
 b. for a peaked tympanogram with low compliance, an indicator as otosclerosis,
 c. for a flat tympanogram with low compliance, an indicator as a fluid filled tympanic cavity, and
 d. for a tympanogram with maximum compliance shifted in the negative pressure range, an indicator as Eustachian tube dysfunction.

13. A method for automatically assessing loss of hearing sensitivity and loss of compression with user defined frequency resolution by means of extrapolated OAE I/O-functions and ABRs as well as for automatically fitting hearing aids according to claim 2, including in addition to the conducting and recording of OAE and ABR I/O-functions TEOAE, DPOAE, and ABR hearing screenings, displaying respective "pass/refer" responses.

14. A method for automatically assessing loss of hearing sensitivity and loss of compression with user defined frequency resolution by means of extrapolated OAE I/O-functions and ABRs as well as for automatically fitting hearing aids according to claim 1, including generating and measuring DPOAE at different stimulus levels within an entire dynamic range of electro-acoustic transducers and at different frequencies wherein the frequency resolution is equal to or higher than the frequency resolution known from of the clinical audiogram for obtaining OAE I/O-functions that mirror the non-linear compressive sound processing at different cochlear sites.

15. A method for automatically assessing loss of hearing sensitivity and loss of compression with user defined frequency resolution by means of extrapolated OAE I/O-functions and ABRs as well as for automatically fitting hearing aids according to claim 14, including extrapolating DPOAE I/O-functions for estimating stimulus levels necessary for generating cochlear responses at the subject's threshold and at stimulus levels out of an electro-acoustic transducer's dynamic range.

16. A method for automatically assessing loss of hearing sensitivity and loss of compression with user defined frequency resolution by means of extrapolated OAE I/O-functions and ABRs as well as for automatically fitting hearing aids according to claim 15, including optionally recording and separating TEOAE I/O-functions in different frequency specific TEOAE-components representing cochlear responses at different sites in the cochlea and plotted in a semi logarithmic plot and curve fitted by linear regression analysis or any other curve fitting procedures using the intersection of the regression line with the stimulus level axis as an estimate for the stimulus level which would generate a TEOAE at the subject's hearing threshold.

17. A method for automatically assessing loss of hearing sensitivity and loss of compression with user defined frequency resolution by means of extrapolated OAE I/O-functions and ABRs as well as for automatically fitting hearing aids according to claim 16, including using the slope s and/or the compression factor k=1/s of the frequency specific TEOAE I/O-functions at selected frequencies to provide the compression profile $k(f_2)$ for matching hearing aid fitting parameters.

18. A method for automatically assessing loss of hearing sensitivity and loss of compression with user defined frequency resolution by means of extrapolated OAE I/O-functions and ABRs as well as for automatically fitting hearing aids according to claim 15, including plotting an estimated hearing threshold in the form of the clinical audiogram.

19. A method for automatically assessing loss of hearing sensitivity and loss of compression with user defined frequency resolution by means of extrapolated OAE I/O-functions and ABRs as well as for automatically fitting hearing aids according to claim 18, wherein the estimated hearing threshold is plotted in the form of the clinical audiogram in which hearing loss classes are indicated for classifying hearing loss at tested frequencies.

20. A method for automatically assessing loss of hearing sensitivity and loss of compression with user defined frequency resolution by means of extrapolated OAE I/O-functions and ABRs as well as for automatically fitting hearing aids according to claim 19, wherein the corresponding area of maximum hearing loss is marked and/or high-lighted in a manner to provide comment on the degree of hearing loss in addition to the hearing threshold.

21. A method for automatically assessing loss of hearing sensitivity and loss of compression with user defined frequency resolution by means of extrapolated OAE I/O-functions and ABRs as well as for automatically fitting hearing aids according to claim 15, including extrapolating the hearing threshold to higher or lower audiogram frequencies by using estimated hearing threshold values at frequencies between the audiogram frequencies.

22. A method for automatically assessing loss of hearing sensitivity and loss of compression with user defined frequency resolution by means of extrapolated OAE I/O-functions and ABRs as well as for automatically fitting hearing aids according to claim 14, including eliciting DPOAE I/O-functions using a primary tone level setting that accounts for the a different suppression of the two primary tones at the DPOAE generation site of the cochlea plotted in a semilogarithmic plot; and fitted by linear regression analysis using the an intersection of the a regression line with a stimulus level axis as an estimate for the stimulus level to generate a DPOAE at the subject's hearing threshold.

23. A method for automatically assessing loss of hearing sensitivity and loss of compression with user defined frequency resolution by means of extrapolated OAE I/O-functions and ABRs as well as for automatically fitting hearing aids according to claim 22, including fitting the DPOAE I/O-functions by weighted Least Mean Square Extrapolation regression analysis using independent weighting factors.

24. A method for automatically assessing loss of hearing sensitivity and loss of compression with user defined frequency resolution by means of extrapolated OAE I/O-functions and ABRs as well as for automatically fitting hearing aids according to claim 14, wherein a correlation coefficient gives a measure of accuracy of a fit for evaluating the accuracy of hearing threshold estimation and can be used as a criterion for repeating or rejecting measurement if it is smaller than a defined value; and user defined slope values, and/or predetermined minimum values within the I/O-function provide objective criteria for repeating or rejecting measurements.

25. A method for automatically assessing loss of hearing sensitivity and loss of compression with user defined frequency resolution by means of extrapolated OAE I/O-functions and ABRs as well as for automatically fitting hearing aids according to claim 14, wherein an estimated stimulus level which would elicit a cochlea response at the hearing threshold is used for estimating hearing loss.

26. A method for automatically assessing loss of hearing sensitivity and loss of compression with user defined frequency resolution by means of extrapolated OAE I/O-functions and ABRs as well as for automatically fitting hearing aids according to claim 14, including employing OAE I/O functions for assessing cochlear compression wherein the slope s and/or the compression factor k=1/s of the DPOAE-function at selected $f_2$ frequencies provides the compression profile $k(f_2)$ for matching hearing aid fitting parameters.

27. A method for automatically assessing loss of hearing sensitivity and loss of compression with user defined frequency resolution by means of extrapolated OAE I/O-functions and ABRs as well as for automatically fitting hearing aids according to claim 14, including delivering additional acoustic stimuli in the outer ear canal in order to suppress secondary responses generated below and above a cochlea site providing primary responses.

28. A method for automatically assessing loss of hearing sensitivity and loss of compression with user defined frequency resolution by means of extrapolated OAE I/O-functions and ABRs as well as for automatically fitting hearing aids according to claim 1, including performing the calibration of the sound pressure in the ear canal after inserting the sound probe automatically to check the sound probe's seal; and estimating volume and length of the subject's ear canal.

29. A method for automatically assessing loss of hearing sensitivity and loss of compression with user defined frequency resolution by means of extrapolated OAE I/O-functions and ABRs as well as for automatically fitting hearing aids according to claim 1, including displaying on a screen a notice indicating, after the sound probe's seal is checked by analysing the pattern of the frequency response and in the event of insufficient seal where sound pressure at low frequencies is below a distinct value, for a tester to replace the sound probe by a graph on the screen.

30. A method for automatically assessing loss of hearing sensitivity and loss of compression with user defined frequency resolution by means of extrapolated OAE I/O-functions and ABRs as well as for automatically fitting hearing aids according to claim 1, including calculating sound pressure at the eardrum for selected frequencies from the estimated individual ear canal length and volume by determining sound pressure maxima in the frequency response and estimates of middle ear/inner ear impedance measured or estimated using mathematical models in order to control a loudspeaker's voltage for generating defined sound pressure in the front of the eardrum.

31. A method for automatically assessing loss of hearing sensitivity and loss of compression with user defined frequency resolution by means of extrapolated OAE I/O-functions and ABRs as well as for automatically fitting hearing aids according to claim 1, including employing a switch selector to start alternatively
- (i) assessment of cochlear sensitivity and compression by means of OAE,
- (ii) assessment of cochlear sensitivity and compression by means of ABR,
- (iii) automatic non-cooperative hearing aid fitting according,
- (iv) new born hearing screening methods with "pass/refer" responses,
- (v) detection of neural disorders,
- (vi) determination of middle-ear status, and
- (vii) stop measurement.

32. A method for automatically assessing loss of hearing sensitivity and loss of compression with user defined frequency resolution by means of extrapolated OAE I/O-functions and ABRs as well as for automatically fitting hearing aids according to claim 31, wherein the switch selected primary measuring procedures automatically initiates secondary measuring procedures, depending on user defined criteria.

33. A method for automatically assessing loss of hearing sensitivity and loss of compression with user defined frequency resolution by means of extrapolated OAE I/O-functions and ABRs as well as for automatically fitting hearing aids according to claim 32, including classifying and displaying the results of switch selected primary measuring procedures and secondary measuring procedures by type and degree of hearing loss.

34. A method for automatically assessing loss of hearing sensitivity and loss of compression with user defined frequency resolution by means of extrapolated OAE I/O-functions and ABRs as well as for automatically fitting hearing aids according to claim 33, including displaying on a screen the results from DPOAE Cochlea-Scan and ABR Cochlea-Scan measurements as follows:
- a. in the event of estimated hearing loss being lower than 15 dB for all frequencies, the indicator "normal hearing",
- b. in the event of estimated hearing loss being more than 15 dB HL and lower than 25 dB HL for at least one frequency, the indicator "slight hearing loss",
- c. in the event of estimated hearing loss being more than 25 dB HL and lower than 30 dB HL for at least one frequency, the indicator "mild hearing loss",
- d. in the event of estimated hearing loss being more than 30 dB HL and lower than 50 dB HL for at least one frequency, the indicator "moderate hearing loss",
- e. in the event of estimated hearing loss being more than 50 dB HL and lower than 70 dB HL for at least one frequency, the indicators "severe hearing loss", and
- f. in the event of estimated hearing loss being more than 70 dB HL for at least one frequency, the indicators "profound hearing loss".

35. A method for automatically assessing loss of hearing sensitivity and loss of compression with user defined frequency resolution by means of extrapolated OAE I/O-functions and ABRs as well as for automatically fitting hearing aids according to claim 34, wherein during measurement sequence, the "stop" switch in the "switch select" status displays an inquiry for the tester to return to "switch select" status, if desired.

36. A method for automatically assessing loss of hearing sensitivity and loss of compression with user defined frequency resolution by means of extrapolated OAE I/O-functions and ABRs as well as for automatically fitting hearing aids according to claim 34, including performing the following switching sequences:
- i) in the case of "normal hearing", returning to the "switch select" status,
- ii) in the case of "slight hearing loss", returning to the "switch select" status or performing a tympanometry measurement,
- iii) in the case of "mild hearing loss" and "moderate hearing loss", performing a tympanometry measurement, and
- iv) in the case of estimated hearing loss more than 50 dB HL, performing an ABR Cochlea Scan measurement.

37. A method for automatically assessing loss of hearing sensitivity and loss of compression with user defined frequency resolution by means of extrapolated OAE I/O-functions and ABRs as well as for automatically fitting hearing aids according to claim 36, including initiating a tympanometry measurement when ABR Cochlea-Scan measurement results show a hearing loss lower than 70 dB HL, and returning to "switch select" status when the ABR Cochlea-Scan measurement results in a hearing loss higher than 70 dB HL display "profound hearing loss".

38. A method for automatically assessing loss of hearing sensitivity and loss of compression with user defined frequency resolution by means of extrapolated OAE I/O-functions and ABRs as well as for automatically fitting hearing aids according to claim 36, including displaying when tympanometry measurements reveal middle-ear disorder "middle ear affected", or if normal middle ear functions, "middle ear not affected"; and performing in both cases an ABR Inter-Peak-Latency measurements, and in the case of normal inter-peak-latency displaying "Auditory nerve (AN) not affected", and in the case of abnormal inter-peak-latency displaying "Auditory Nerve affected".

39. A method for automatically assessing loss of hearing sensitivity and loss of compression with user defined frequency resolution by means of extrapolated OAE I/O-functions and ABRs as well as for automatically fitting hearing aids according to claim 31, including initiating ABR Cochlea-Scan measurements with the following "switch select" Cochlea-Scans, Automatic Non-Cooperative (ANC) Hearing Aid Fitting, Screening, and Differential of middle ear, cochlear, neural disorder measurements and corresponding secondary measurement sequences:
- a. for "normal hearing, initiating" the switch "stop" sequence,
- b. for "slight hearing loss", performing a user defined sequence wherein either initiating the "stop" sequence, or performing a tympanometry testing sequence;
- c. if the tympanometry results show "normal", displaying a "middle ear not affected" and either initiating the switch "stop" sequence, or performing an ABR Inter-Peak-Latency (IPL) testing sequence;
- d. if the tympanometry results are not "normal", displaying a "Middle ear affected", and either initiating the "stop" sequence, or performing the ABR IPL testing sequence;
- e. if the IPL is normal, displaying an "AN not affected" and initiating the switch "stop" sequence; and
- f. if the IPL is not normal, displaying "AN affected".

40. A method for automatically assessing loss of hearing sensitivity and loss of compression with user defined frequency resolution by means of extrapolated OAE I/O-functions and ABRs as well as for automatically fitting hearing aids according to claim 31, including starting screening measurements during the "switch select" status sequence, which initiate corresponding secondary measurements by fixing electrodes, measuring and checking electrode impedance, estimating ear canal length, calculating middle ear impedance by measurement or model, correcting sound pressure, and applying defined pressure at the ear drum, measuring ABR, high click rate ABR and AMFR, applying pattern recognition to determine ABR/AMFR threshold levels, converting threshold levels to hearing loss, and classifying hearing loss and type

41. A method for automatically assessing loss of hearing sensitivity and loss of compression with user defined frequency resolution by means of extrapolated OAE I/O-functions and ABRs as well as for automatically fitting hearing aids according to claim 31, including employing Tympanometry measurements, which when started during "switch select" status, initiate corresponding secondary measurements.

42. A method for automatically assessing loss of hearing sensitivity and loss of compression with user defined frequency resolution by means of extrapolated OAE I/O-functions and ABRs as well as for automatically fitting hearing aids according to claim 31, including employing ABR Inter-Peak-Latency (IPL) measurements, which, when started during "switch select" status sequence, initiate corresponding secondary measurements.

43. A method for automatically assessing loss of hearing sensitivity and loss of compression with user defined frequency resolution by means of extrapolated OAE I/O-functions and ABRs as well as for automatically fitting hearing aids according to claim 31, including displaying on a screen reconstructed audiograms, the degree of hearing loss by highlighting them with respective comment proximate the affected area in the audiogram, a status of measurement corresponding to that chosen during "switch select" status sequence, and the status of the sound probe and electrodes.

* * * * *